US011530383B2

(12) United States Patent
Bosmans et al.

(10) Patent No.: US 11,530,383 B2
(45) Date of Patent: Dec. 20, 2022

(54) BIOCONTROL ORGANISM

(71) Applicants: Katholieke Universiteit Leuven, Leuven (BE); Nederlands Instituut Voor Ecologie (NIOOKNAW), Wageningen (NL); Scientia Terrae VZW, Sint-Katelijne Waver (BE); Proefstation Groenteteelt, Sint-Katelijne-Waver (BE); Proefstation Hoogstraten, Meerle (BE)

(72) Inventors: Lien Bosmans, Mortsel (BE); Bart Lievens, Geel (BE); Hans Rediers, Kortenaken (BE); Jos Raaijmakers, Rhenen (NL); Irene De Bruijn, Breda (NL)

(73) Assignees: KATHOLIEKE UNIVERSITEIT LEUVEN, Leuven (BE); NEDERLANDS INSTITUTE OF ECOLOGY (NIOO-KNAW), Wageningen (NL); SCIENTIA TERRAE VZW, Sint Katelijne (BE); PROEFSTATION GROENTETEELT, Sint Katelijne (BE); PROEFCENTRUM HOOGSTRATEN, Meerle (BE)

( * ) Notice: Subject to any disclaimer, the term of this patent is extended or adjusted under 35 U.S.C. 154(b) by 410 days.

(21) Appl. No.: 16/472,630

(22) PCT Filed: Dec. 22, 2017

(86) PCT No.: PCT/EP2017/084394
§ 371 (c)(1),
(2) Date: Jun. 21, 2019

(87) PCT Pub. No.: WO2018/115445
PCT Pub. Date: Jun. 28, 2018

(65) Prior Publication Data
US 2019/0357541 A1    Nov. 28, 2019

(30) Foreign Application Priority Data

Dec. 23, 2016  (GB) ..................... 1622086

(51) Int. Cl.
| C12N 1/20 | (2006.01) |
| A01N 63/25 | (2020.01) |
| C12R 1/01 | (2006.01) |
| C12R 1/07 | (2006.01) |

(52) U.S. Cl.
CPC ............. *C12N 1/205* (2021.05); *A01N 63/25* (2020.01); *C12N 1/20* (2013.01); *C12R 2001/01* (2021.05); *C12R 2001/07* (2021.05)

(58) Field of Classification Search
CPC .......... C12N 1/205; C12N 1/20; A01N 63/25; C12R 2001/01
See application file for complete search history.

(56) References Cited

U.S. PATENT DOCUMENTS

2016/0278388 A1    9/2016  Beau et al.

FOREIGN PATENT DOCUMENTS

| CN | 105733990 A | 7/2016 |
| EP | 1788074 A1 | 8/2007 |
| WO | 2011139672 A1 | 11/2011 |
| WO | 2014210372 A1 | 12/2014 |
| WO | 2015100431 A2 | 7/2015 |
| WO | 2015100432 A2 | 7/2015 |

OTHER PUBLICATIONS

Pandya et al., Microbiology, 2015, vol. 84, No. 1, pp. 80-89, published online on Feb. 4, 2015.*
NCBI information regarding Paenibacillus xylanilyticus strain, Gen Bank accession No. JX280508.1, retrieved from NCBI on Dec. 15, 2021, 2 pages of PDF.*
Meriam-Webster dictionary, definition of prevent, retrieved from Meriam Webster Dictionary online on Dec. 15, 2021, 1 page.*
Search result for DSM15478 in German Collection of Microorganisms and Cell Cultures GmbH, retrieved on Apr. 19, 2022, 2 pages of PDF.*
Tamura, et al., "MEGA5: Molecular Evolutionary Genetics Analysis Using Maximum Likelihood, Evolutionary Distance, and Maximum Parsimony Methods", Mol. Biol. Evol., pp. 2731-2739, 2011.
Ridder-Duine, et al., "Rhiaosphere bacterial community composition in natural stands of *Carex arenaria* (sand sedge) is determined by bulk soil community composition", Soil Biology & Biochemistry, pp. 349-357, 2005.
International Search Report dated May 7, 2018, in reference to co-pending European Patent Application No. PCT/EP2017/084394.
Castanheira, et al., "Annual ryegrass-associated bacteria with potential for plant growth promotion", Microbiological Research, Fischer, Jena, DE, vol. 169, No. 9, Jan. 8, 2014, pp. 768-779, XP029006641.
Vaninsberghe, et al., "Isolation of a Substantial Proportion of Forest Soil Bacterial Communities Detected via Pyrotag Sequencing", Applied and Environmental Microbiology, Mar. 15, 2013 (Mar. 15, 2013), p. 2096, XP055468379.

(Continued)

*Primary Examiner* — Kade Ariani
(74) *Attorney, Agent, or Firm* — Dinsmore & Shohl, LLP

(57) ABSTRACT

The present invention provides methods to improve the health and vigor, including enhancement of the growth of plants, including important crop plants. In particular, the present invention provides methods of treating or preventing a rhizogenic or tumorigenic plant disease caused by bacteria, comprising administering to the plant an effective amount of at least one isolated *Paenibacillus* strain or of an extract of at least one isolated *Paenibacillus* strain, wherein said at least one *Paenibacillus* strain comprises a 16S rRNA sequence with at least 93% sequence identity to the sequence of SEQ ID NO: 1.

4 Claims, 4 Drawing Sheets
Specification includes a Sequence Listing.

(56) References Cited

OTHER PUBLICATIONS

Lorentz, et al., "Evaluation of antimicrobial activity in *Paenibacillus* spp. strains isolated from natural environment", Letters in Applied Microbiology, vol. 43, No. 5, Nov. 1, 2006 (Nov. 1, 2006), pp. 541-547, XP055455658.
Bosmans, et al., "Potential for Biocontrol of Hairy Root Disease by a Paenibacillus Clade", Frontiers in Microbiology, vol. 8, Jan. 1, 2017, XP055455664.
Duran, et al., "Endophytic bacteria from selenium-supplemented wheat plants could be useful for plant-growth promotion, biofortification and Gaeumannomyces graminis biocontrol in wheat production", Biology and Fertility of Soils, vol. 50, No. 6, May 6, 2014 (May 6, 2014), pp. 983-990, XP055468385.
German Search Report in reference to co-pending German Application No. GB1622086.5 filed Oct. 16, 2017.
Haggag, et al., "Colonization of peanut roots by biofilm-forming Paenibacillus polymyxa initiates biocontrol against crown rot disease", Journal of Applied Microbiology, pp. 961-969, 2008.
Bosmans, et al "Potential for Biocontrol of Hairy Root Disease by a Paenibacillus clade exhibiting antagonistic activity against rhizogenix Agrobacterium biovar 1 strains", Frontier in Microbiology, pp. 1-37, Nov. 2016.
Son, et al., "Plant growth-promoting rhizobacteria, Paenibacillus polymyxa and Paenibacillus lentimorbus suppress disease complex caused by root-knot nematode and fusarium wilt fungus", Journal of Applied Microbiology, pp. 524-532, 2009.
Lal, et al., "Ecology and biotechnological potential of Paenibacillus polymyxa: a minireview", Indian J. Micrboial, pp. 2-9, Mar. 2009.
Nelson, et al., "*Paenibacillus tundrae* sp. nov. and *Paenibacillus xylanexedens* sp. nov., psychrotolerant, xylan-degrading bacteria from Alaska tundra", International Journal of Systematic and Evolutionary Microbiology, pp. 1708-1714, 2009.
Sato, et al., "Suppressive Potential of Paenibacillus Strains Isolated from the Tomato Phyllosphere against Fusarium Crown and Root Rot of Tomato", Microbes and Environments, vol. 29, No. 2, pp. 168-177, 2014.
Tyc, et al., "Impact of interspecific interactions on antimicrobial activity among soil bacteria", Frontiers in Microbiology, vol. 5, Article 567, pp. 1-10, Oct. 2014.
Wei-Wei, et al., "Antagonistic Activities of Volatiles from Four Strains of *Bacillus* spp. and *Paenibacillus* spp. Against Soil-Borne Plant Pathogens", Agricultures Sciences in China, pp. 1104-1114, 2008.

\* cited by examiner

SEQUENCE LISTING

<160> NUMBER OF SEQ ID NOS: 23

<210> SEQ ID NO 1
<211> LENGTH: 38
<212> TYPE: DNA
<213> ORGANISM: Artificial Sequence
<220> FEATURE:
<223> OTHER INFORMATION: Synthetic Construct

<400> SEQUENCE: 1
ttgggacaac taccggaaac ggtagctaat accgaata                              38

<210> SEQ ID NO 2
<211> LENGTH: 91
<212> TYPE: DNA
<213> ORGANISM: Artificial Sequence
<220> FEATURE:
<223> OTHER INFORMATION: Synthetic Construct

<400> SEQUENCE: 2
cacgtaggca acctgccctc aagcttggga caactaccgg aaacggtagc taataccgaa      60
tagttgtttt cttctcctga agagaactgg a                                    91

<210> SEQ ID NO 3
<211> LENGTH: 91
<212> TYPE: DNA
<213> ORGANISM: Artificial Sequence
<220> FEATURE:
<223> OTHER INFORMATION: Synthetic Construct

<400> SEQUENCE: 3
cacgtaggca acctgccctc aagcttggga caactaccgg aaacggtagc taataccgaa      60
tacttgcttc cttcgcctga aggaagctgg a                                    91

<210> SEQ ID NO 4
<211> LENGTH: 91
<212> TYPE: DNA
<213> ORGANISM: Artificial Sequence
<220> FEATURE:
<223> OTHER INFORMATION: Synthetic Construct

<400> SEQUENCE: 4
cacgtaggca acctgccctc aagcttggga caactaccgg aaacggtagc taataccgaa      60
tacttgcttc tttcgcctga aggaagctgg a                                    91

<210> SEQ ID NO 5
<211> LENGTH: 91
<212> TYPE: DNA
<213> ORGANISM: Artificial Sequence
<220> FEATURE:
<223> OTHER INFORMATION: Synthetic Construct

<400> SEQUENCE: 5
cacgtaggca acctgccctc aagtttggga caactaccgg aaacggtagc taataccgaa      60
taattgtttt cttcgcctga agggaactgg a                                    91

<210> SEQ ID NO 6
<211> LENGTH: 91
<212> TYPE: DNA
<213> ORGANISM: Artificial Sequence
<220> FEATURE:
<223> OTHER INFORMATION: Synthetic Construct

<400> SEQUENCE: 6
cacgtaggca acctgccctc aagtttggga caactaccgg aaacggtagc taataccgaa    60
tagttgtttt cttcgcctga agagaactgg a                                    91

<210> SEQ ID NO 7
<211> LENGTH: 91
<212> TYPE: DNA
<213> ORGANISM: Artificial Sequence
<220> FEATURE:
<223> OTHER INFORMATION: Synthetic Construct

<400> SEQUENCE: 7
cacgtaggca acctgccctc aagtttggga caactaccgg aaacggtagc taataccgaa    60
tagttgtttt cttctcctga agagaactgg g                                    91

<210> SEQ ID NO 8
<211> LENGTH: 91
<212> TYPE: DNA
<213> ORGANISM: Artificial Sequence
<220> FEATURE:
<223> OTHER INFORMATION: Synthetic Construct

<400> SEQUENCE: 8
cacgtaggca acctgccctc aagtttggga caactaccgg aaacggtagc taataccgaa    60
tagttgtttt cttctcctga agagaactgg a                                    91

<210> SEQ ID NO 9
<211> LENGTH: 91
<212> TYPE: DNA
<213> ORGANISM: Artificial Sequence
<220> FEATURE:
<223> OTHER INFORMATION: Synthetic Construct

<400> SEQUENCE: 9
cacgtaggca acctgcccac aagacaggga taactaccgg aaacggtagc taataccga    60 tacatccttt tcctgcatgg gagaaggagg a                                    91

<210> SEQ ID NO 10
<211> LENGTH: 91
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (84)..(84)
<223> OTHER INFORMATION: n is a, c, g, or t

<400> SEQUENCE: 10
cacgtaggca acctgccctc aagactggga taactaccgg aaacggtagc taataccgga    60
taatttatta catagcatta tgtnataatg a                                    91

<210> SEQ ID NO 11
<211> LENGTH: 91
<212> TYPE: DNA
<213> ORGANISM: Artificial Sequence
<220> FEATURE:
<223> OTHER INFORMATION: Synthetic Construct

<400> SEQUENCE: 11
cacgtaggca acctgccctc aagactggga taactaccgg aaacggtagc taataccgga    60
taatttcttt cctctcctga agagagaatg a    91

<210> SEQ ID NO 12
<211> LENGTH: 91
<212> TYPE: DNA
<213> ORGANISM: Artificial Sequence
<220> FEATURE:
<223> OTHER INFORMATION: Synthetic Construct

<400> SEQUENCE: 12
cacgtaggca acctaccctc tagactggga taactaccgg aaacggtagc taataccgga    60
taattccctg accccctgg gctagggatg a    91

<210> SEQ ID NO 13
<211> LENGTH: 91
<212> TYPE: DNA
<213> ORGANISM: Artificial Sequence
<220> FEATURE:
<223> OTHER INFORMATION: Synthetic Construct

<400> SEQUENCE: 13
cacgtaggta acctgcctgt aagactggga taactaccgg aaacggtagc taataccgga    60
taatttgttt cttctcatga agagacactg a    91

<210> SEQ ID NO 14
<211> LENGTH: 91
<212> TYPE: DNA
<213> ORGANISM: Artificial Sequence
<220> FEATURE:
<223> OTHER INFORMATION: Synthetic Construct

<400> SEQUENCE: 14
cacgtaggta acctgcctat aagactggga taactaccgg aaacggtagc taataccgga    60
taatttattt cttctcatga agagatactg a    91

<210> SEQ ID NO 15
<211> LENGTH: 91
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (84)..(84)
<223> OTHER INFORMATION: n is a, c, g, or t

<400> SEQUENCE: 15
cacgtaggca acctgcccgt aagaccggga taactaccgg aaacggtagc taataccgga    60
taatcaagtc ttccgcatgg gagncttggg a    91

<210> SEQ ID NO 16
<211> LENGTH: 91
<212> TYPE: DNA
<213> ORGANISM: Artificial Sequence
<220> FEATURE:
<223> OTHER INFORMATION: Synthetic Construct

<400> SEQUENCE: 16
cacgtaggca acctgcctgc aagaccggga tacccacgg aaacgtgagc taataccgga    60
tatctcattt cctctcctga ggggatgatg a    91

<210> SEQ ID NO 17
<211> LENGTH: 91
<212> TYPE: DNA
<213> ORGANISM: Artificial Sequence
<220> FEATURE:
<223> OTHER INFORMATION: Synthetic Construct

<400> SEQUENCE: 17
tacgtaggta acctgcccctt aagactggga taactcacgg aaacgtgggc taataccgga    60
tagtcgattt cctcgcatga gggaatcggg a    91

<210> SEQ ID NO 18
<211> LENGTH: 91
<212> TYPE: DNA
<213> ORGANISM: Artificial Sequence
<220> FEATURE:
<223> OTHER INFORMATION: Synthetic Construct

<400> SEQUENCE: 18
cacgtaggca acctgccctc aagactggga taacctccgg aaacggatgc taataccgga    60
tatgcggtct ctcctcctgg agggatcggg a    91

<210> SEQ ID NO 19
<211> LENGTH: 91
<212> TYPE: DNA
<213> ORGANISM: Artificial Sequence
<220> FEATURE:
<223> OTHER INFORMATION: Synthetic Construct

<400> SEQUENCE: 19
cacgtgggta acctgcccat aagactggga taacattcgg aaacgaatgc taataccgga    60
tacgcaattt ggtcgcatgg ccgarttggg a    91

<210> SEQ ID NO 20
<211> LENGTH: 90
<212> TYPE: DNA
<213> ORGANISM: Artificial Sequence
<220> FEATURE:
<223> OTHER INFORMATION: Synthetic Construct

<400> SEQUENCE: 20
acgtgggtaa cctgcccata agactgggat aacattcgga aacgaatgct aataccggat    60
acgcgaatcg gtcgcatgat cgaatcggga    90

<210> SEQ ID NO 21
<211> LENGTH: 91
<212> TYPE: DNA
<213> ORGANISM: Artificial Sequence
<220> FEATURE:
<223> OTHER INFORMATION: Synthetic Construct

<400> SEQUENCE: 21
cacgtaggca acctgcctgt aagaccggga taacttgcgg aaacgtgagc taataccgga    60
taactggttt cttcgcatga agaagtcatg a    91

<210> SEQ ID NO 22

```
<211> LENGTH: 91
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 22
cacgtaggtn anctgcctat aagatcggga taactatcgg aaacgatagc taagaccgga      60
taattggttt nctcgcatga gagaactatg a                                    91

<210> SEQ ID NO 23
<211> LENGTH: 91
<212> TYPE: DNA
<213> ORGANISM: Artificial Sequence
<220> FEATURE:
<223> OTHER INFORMATION: Synthetic Construct

<400> SEQUENCE: 23
acgtaggcaa cctgcctgta agatcgggat aactaccgga aacggtagct aagaccggat      60
agctggtttc tccgcatggg ggaatcatga a                                    91
```

BIOCONTROL ORGANISM

FIELD OF THE INVENTION

The present invention relates to the biological control of plant diseases such as crown gall disease and hairy root disease using specific *Paenibacillus* strains.

BACKGROUND OF THE INVENTION

Conventional pest control technologies based on the use of agricultural chemicals have contributed to efficient agricultural productivity. However, their use also has led to increasing public concerns regarding their negative impacts on the environment. Environmentally-beneficial agriculture using no or reduced amounts of agricultural chemicals and satisfying cultivation efficiency, while assuring human safety is desired and necessary. Therefore, pest and disease control technology fulfilling such demand is needed in the art.

Crops in different ecosystems around the world may suffer less than ideal conditions due to soil or weather conditions, or various stresses, as well as diseases that can negatively affect the health and vigor of the crop plants. Such factors can reduce productivity of the crops to a greater or lesser degree, even under good growing conditions. Thus, crop plants can benefit from treatment that will increase the health and vigor of the plants, whether the plants are stressed by poor conditions, by disease, or even when the plants are healthy or grown under favorable conditions.

A number of plant diseases have negative effects on crop plants worldwide. Microbial plant pathogens can lead to losses in yield, and can even kill crop plants. Therefore, strategies to improve plant defenses against pathogens are needed to improve cultivation, crop yield, and crop quality, while avoiding environmental pollution of the plants and the soil in which they are grown. Biological approaches, such as the use of beneficial bacteria as described herein, therefore are helpful to improve crop plant health generally, and to reduce the effects of plant pathogens. Since the early 1990s, in several European countries hydroponically grown cucumber plants and tomato crops have been affected by a disorder called "hairy root disease" (HRD). The disease is characterized by extensive root proliferation leading to strong vegetative growth and, in severe cases, substantial losses in marketable yield. In hydroponic crops HRD is generally associated with rhizogenic *Agrobacterium* biovar 1 strains (further also referred to as "rhizogenic agrobacteria"), harbouring an Ri-plasmid (root-inducing plasmid). Symptoms arise following transfer of a portion of the Ri-plasmid (T-DNA; transferred DNA) from the bacterium to plant cells, where it is integrated in the chromosomal DNA and subsequently, leading to excessive root development. Consequently, HRD cannot be controlled by curative means and rather preventative actions should be taken, such as preventing and/or removing *Agrobacterium* containing biofilms that are often associated with the disease in the greenhouse irrigation system. However, to effectively prevent the disease generally high concentrations of chemical disinfectants are required, including levels that may be phytotoxic (Bosmans et al. 2016c). Moreover, several of these chemicals may be converted to unwanted by-products with human health hazards. Therefore, there is currently a strong interest in alternative means to prevent and control HRD, such as the use of biocontrol organisms (BCO).

The use of BCO has received great attention the last few decades because of the ability of such antagonistic strains to suppress plant diseases with less environmental impact than chemical pesticides, their high specificity and the possibility to be integrated with other control methods. Especially rhizosphere bacteria are generally considered ideal BCO of soilborne pathogens because of their rapid growth and fast colonization rate of the rhizosphere providing a front-line defense against pathogen attack, their versatility to protect plants under different conditions, and production of antimicrobial compounds.

Lorenz et al. (2006) Lett. Appl. Microbiol. 43, 541-547, describe certain *Paenibacillus* strains with antibacterial activity against *Citrobacter freundii Enterobacter cloacae, Pseudomonas putida, Ralstonia solanacearum, Salmonella tiphymurium, Listeria monocytogenes, Burkolderia cepacia; Pectobacterium carotovorum* ssp. *Brasilensis, Shigella sonnei; Listeria innocua; Pseudomonas fluorescens, Staphylococcus aureus, Pectobacterium carotovorum Xanthomonas anoxopodis*.

Son et al. (2009) J. Appl. Microbiol. 107, 524-532 describe *Paenibacillus polymyxa* and *Paenibacillus lentimorbus* with activity against root-knot nematode and fusarium wilt fungus.

Haggag & Timmusk (2008) J. Appl. Microbiol. 104, 961-969 disclose the use of *Paenibacillus polymyxa* against crown rot caused by the yeast *Aspergillus niger*.

Sato et al. (2014) Microbes Environ. 29, 168-177 disclose the use of *Paenibacillus* strains against Fusarium oxysporum causing crown and root rot in tomatoes.

Nelson et al. (2009) Int. J. System. Evol. Microbiol. 59, 1708-1714 disclose the psychrotolerant xylan-degrading bacteria *P. tundrae* sp. nov. and *P. xylanexedens* sp. nov.

EP1788074 discloses strains *Paenibacillus* sp. BS-0048, *Paenibacillus* sp. BS-0074, *Paenibacillus polymyxa* BS-0105, *Paenibacillus* sp. BS-0277.

CN105733990 discloses a *Paenibacillus* strain with activity against *Gibberella fujikuroi, Fusariurium oxysporum, Sphaerotheca fuliginea* and flax root rot.

US20160278388 discloses fungicidal *Paenibacillus* sp. strains with mutant fusaricidin synthetase genes.

Tyc et al. (2014) Front Microbiol. 5, 567, describe an assay to analyse the antimicrobial effect of various microorganisms, including *Paenibacillus* strains on *E. coli* and *S. aureus* and its effect on plant pathogens.

Wei-wei et al. (2008) Agric. Sci. China 7, 1104-1114 disclose antagonistic activities of volatiles from four strains of *Bacillus* spp. and *Paenibacillus* spp. against soil-borne plant pathogenic fungi.

Lal & Tabacchioni (2014) Front Microbiol. 28, 567 is a review on the biotechnological potential of *Paenibacillus polymyxa*.

There is nevertheless a need for an effective treatment by BCO to combat diseases such as hairy root disease and crown gall disease.

SUMMARY OF THE INVENTION

There is a need in the art for pest and disease control technology with less environmental impact than chemical pesticides.

The present invention relates in general to the use of biocontrol organisms for improving the health and disease resistance of plants, including important crop plants such as eggplant, cucumber, tomato and others.

The embodiments of the invention described herein are provided for the control of crop pathogens such as HRD and to improve plant health and vigor, including germination, growth, disease resistance, and improvement of crop quality and quantity.

The present invention is directed to bacteria, bacterial combinations and their metabolites or extracts thereof which can be used in methods to improve the health and vigor, including enhancement of the growth of plants, including important crop plants, while improving the sustainability of the agro-ecosystem. In particular, the present invention relates to the application of an isolated *Paenibacillus* strain or a combination of *Paenibacillus* strains, as herein identified, or their metabolites or extracts in the treatment or prevention of a plant disease, in particular of a rhizogenic or tumorigenic plant disease caused by bacteria, even more in particular of a rhizogenic or tumorigenic plant disease caused by Agrobacteria or *Rhizobium* bacteria. In a further embodiment of the present invention, said plant diseases are caused by Agrobacteria biovar 2 strains or *Rhizobium vitis* strains.

The present invention is particularly related to methods and uses of an isolated *Paenibacillus* strain as herein identified or of an extract of said isolated *Paenibacillus* strain in the treatment and prevention of hairy root disease (HRD) or crown gall disease. In yet a further embodiment, the present invention is related to methods and uses of a combination of isolated *Paenibacillus* strains as herein identified, or of extracts of said combination of isolated *Paenibacillus* strains as herein identified in the treatment and prevention of hairy root disease (HRD) or crown gall disease.

The isolated *Paenibacillus* strains according to the different embodiments of the present invention, are characterized in that they comprises a 16S rRNA sequence with at least 93% sequence identity to the sequence of SEQ ID NO: 1 (ttgggacaactaccggaaacggtagctaataccgaata). In particular, the at least one isolated *Paenibacillus* strain according to the different embodiments of the present invention comprises a 16S rRNA sequence with at least 93%, preferably at least 95%, more preferably at least 98% sequence identity to the sequence of SEQ ID NO: 1. In yet a more preferred embodiment, the isolated *Paenibacillus* strain according to the present invention comprises a 16S rRNA sequence with 93%, 94%, 95%, 96%, 97%, 98%, 99% or 100% sequence identity to the sequence of SEQ ID NO: 1. In still a more preferred embodiment, the isolated *Paenibacillus* strain according to the different embodiments of the invention comprises a 16S rRNA sequence with a 100% sequence identity to the sequence of SEQ ID NO: 1.

The aforementioned *Paenibacillus* strains include *Paenibacillus xylanexedens* DSM15478, *Paenibacillus illinoisensis* DSM11733, *Paenibacillus pabuli* LMG15970, *Paenibacillus xylanexedens* LMG P-29983, *Paenibacillus illinoisensis* LMG P-29984, *Paenibacillus illinoisensis* LMG P-29982, *Paenibacillus xylanexedens* LMG P-29981, *Paenibacillus taichungensis* DSM19942, *Paenibacillus tundrae* DSM21291, *Paenibacillus tylopili* DSM18927, *Paenibacillus xylanilyticus* DSM17255; and combinations thereof, and can be useful as isolated strains or an extract thereof, for prevention of disease or treatment of healthy plants and plants which are susceptible to plant disease. Although the methods and compositions are useful for administration to any plant or seed, preferred plants are those which are commercial crops, for example eggplant, cucumber and tomato. The methods and compositions of embodiments of the invention can ameliorate the effects of plant diseases, including microbial diseases such as hairy root disease (HRD).

The present invention also specifically discloses four novel isolated *Paenibacillus* strains. In one embodiment, an isolated *Paenibacillus xylanexedens* strain is disclosed, said strain deposited under accession number LMG P-29981. In another embodiment, an isolated *Paenibacillus xylanexedens* strains is disclosed, said strain deposited under accession number LMG P-29983. In yet another embodiment, an isolated *Paenibacillus illinoisensis* strain is disclosed, said strain deposited under accession number LMG-P-29982. In still another embodiment, an isolated *Paenibacillus illinoisensis* strain is disclosed, said strain deposited under accession number LMG P-29984. Said strains were deposited with the Belgian Coordinated Collection of Micro-Organisms (BCCM) (Universiteit Gent, L.L. Ledeganckstraat 35,9000 Gent, Belgium) on Dec. 14, 2016, with respective accession numbers LMG P-29981, LMG P-29983, LMG P-29982 and LMG P-29984. LMG P-29981 as deposited by the Nederlands Instituut voor Ecologie (NIOO-KNAW), LMG P-29982, LMG P-29983 and LMG P-29984 were deposited by the Katholieke Universiteit Leuven (KULeuven). In a further embodiment, the present invention also discloses a composition comprising at least one of said isolated *Paenibacillus* strains or an extract of at least one of said isolated *Paenibacillus* strains. In still another embodiment, the present invention is also directed to plant seeds or seedlings coated or inoculated with at least one of said four isolated *Paenibacillus* strains or with a composition comprising at least one of said four isolated *Paenibacillus* strains or an extract of at least one of said four *Paenibacillus* strains.

As is evident from above, said four novel isolated *Paenibacillus* strains are typically characterized in that they have a 16S rRNA sequence with 100% sequence identity to the sequence of SEQ ID NO: 1.

Numbered statements of the invention are:
1. A method of treating or preventing a rhizogenic or tumorigenic plant disease caused by bacteria, comprising administering to the plant an effective amount of at least one isolated *Paenibacillus* strain or of an extract of at least one isolated *Paenibacillus* strain, wherein said at least one *Paenibacillus* strain comprises a 16S rRNA sequence with at least 93% sequence identity to the sequence of SEQ ID NO: 1 (ttgggacaactaccggaaacggtagctaataccgaata).
2. The method of statement 1 wherein the at least one *Paenibacillus* strain comprises a 16S rRNA sequence with at least 95% sequence identity to the sequence of SEQ ID NO: 1.
3. The method of statements 1 or 2 wherein the at least one *Paenibacillus* strain comprises a 16S rRNA sequence with 100% sequence identity to the sequence of SEQ ID NO: 1.
4. A method of improving the health and vigor of a plant suffering from a rhizogenic or tumorigenic plant disease comprising administering to the plant an effective amount of at least one isolated *Paenibacillus* bacterial strain or of an extract of at least one isolated *Paenibacillus* strain, wherein said at least one *Paenibacillus* strain has a 16S rRNA sequence with at least 93% sequence identity to the sequence of SEQ ID NO: 1 and wherein the improvement in health and vigor is one or more of:
   a) improved resistance to disease;
   b) improved ability to defend against disease;
   c) reduction of disease symptoms;
   e) improved crop productivity.

5. The method of any one of statements 1 4, wherein the rhizogenic or tumorigenic plant disease is caused by Agrobacteria or Rhizobia bacteria; in particular caused by Agrobacteria biovar 2 strains or Rhizobia vitis strains.
6. The method of any of the preceding statements, wherein the rhizogenic plant disease is hairy root disease (HRD).
7. The method of any of the statements 1 to 5, wherein the tumorigenic plant disease is crown gall disease.
8. The method of any one of the preceding statements, wherein the at least one *Paenibacillus* strain is selected from the group consisting of *Paenibacillus xylanexedens* having collection number DSM15478, *Paenibacillus illinoisensis* having collection number DSM11733, *Paenibacillus pabuli* having collection number LMG15970, *Paenibacillus xylanexedens* having collection number LMG P-29983, *Paenibacillus illinoisensis* having collection number LMG P-29984, *Paenibacillus illinoisensis* having collection number LMG P-29982, *Paenibacillus xylanexedens* having collection number LMG P-29981, *Paenibacillus taichungensis* having collection number DSM19942, *Paenibacillus tundrae* having collection number DSM21291, *Paenibacillus tylopili* having collection number DSM18927 and *Paenibacillus xylanilyticus* having collection number DSM17255 or a derivative, variant or mutant of any thereof
9. The method according to statement 8, wherein the at least one *Paenibacillus* strain is *Paenibacillus xylanexedens* having collection number DSM15478.
10. The method according to statement 8, wherein the at least one *Paenibacillus* strain is *Paenibacillus illinoisensis* having collection number DSM11733.
11. The method according to statement 8, wherein the at least one *Paenibacillus* strain is *Paenibacillus pabuli* having collection number LMG15970.
12. The method according to statement 8, wherein the at least one *Paenibacillus* strain is *Paenibacillus xylanexedens* having accession number LMG P-29983.
13. The method according to the statement 8, wherein the at least one *Paenibacillus* strain is *Paenibacillus illinoisensis* having accession number LMG P-29984.
14. The method according to statement 8, wherein the at least one *Paenibacillus* strain is *Paenibacillus illinoisensis* having accession number LMG P-29982.
15. The method according to statement 8, wherein the at least one *Paenibacillus* strain is *Paenibacillus xylanexedens* having accession number LMG P-29981.
16. The method according to any of the statements 1 to 3, wherein the at least one *Paenibacillus* strain is *Paenibacillus taichungensis* having collection number DSM19942.
17. The method according to statement 8, wherein the at least one *Paenibacillus* strain is *Paenibacillus tundrae* having collection number DSM21291.
18. The method according to statement 8, wherein the at least one *Paenibacillus* strain is *Paenibacillus tylopili* having collection number DSM18927.
19. The method according to statements 8, wherein the at least one *Paenibacillus* strain is *Paenibacillus xylanilyticus* having collection number DSM17255.
20. The method according to statement 8, wherein the at least one *Paenibacillus* strain is selected from *Paenibacillus xylanexedens* having collection number LMG P-29981, *Paenibacillus xylanexedens* having collection number LMG P-29983, *Paenibacillus illinoisensis* having collection number LMG P-29982, or *Paenibacillus illinoisensis* having collection number LMG P-29984.
21. The method according to statement 21, wherein the at least one *Paenibacillus* strain is selected from *Paenibacillus xylanexedens* having collection number LMG P-29981 or *Paenibacillus xylanexedens* having collection number LMG P-29983.
22. The method according to any of the preceding statements, wherein the plant is a crop plant.
23. The method according to statement 22, wherein the crop plant is selected from the group consisting of eggplant, cucumber plant and tomato plant.
24. The method according to statement 23, wherein the crop plant is a tomato plant.
25. The method according to anyone of the preceding statements, wherein the plant is grown on a tomato rootstock.
26. The method according to any of the preceding statements, wherein the plant is healthy.
27. The method according to any of the preceding statements, wherein the plant is affected by a plant disease or plant disease symptoms.
28. The method according to statement 27, wherein the plant disease is a bacterial disease.
29. The method according to statement 27 or 28, wherein the plant disease is Hairy Root Disease (HRD).
30. The method according to any of the preceding statements, wherein the administering to the plant is by a method selected from the group consisting of: applying directly onto the substrate on which seedlings are grown, adding to the irrigation water, applying to the hydroponics substrate, application to seed, and foliar spraying.
31. The method according to any of the preceding statements, wherein the administering to the plant provides between $10^2$ and $10^{12}$ cfu of the *Paenibacillus* strain per plant.
32. The method according to any of the preceding statements, wherein the administering to the plant provides between $10^6$ and $10^{12}$ cfu of the *Paenibacillus* strain per plant.
33. The method according to any of the preceding statements, wherein the administering to the plant provides at least $10^8$ cfu of the *Paenibacillus* strain per plant.
34. A method of enhancing growth of a plant, the method comprising administering to the plant a bacterial composition with antagonistic activity against *Agrobacterium* biovar 1 for administration to plants, which comprises at least one isolated *Paenibacillus* strain or extract thereof wherein said at least one *Paenibacillus* strain comprises a 16S rRNA sequence with at least 93% sequence identity to the sequence of SEQ ID NO: 1.
35. The method of statement 34 wherein the at least one *Paenibacillus* strain comprises a 16S rRNA sequence with at least 95% sequence identity to the sequence of SEQ ID NO: 1.
36. The method of statements 34 or 35, wherein the at least one *Paenibacillus* strain comprises a 16S rRNA sequence with 100% sequence identity to the sequence of SEQ ID NO: 1.
37. A method of treating a plant disease in a plant in need thereof, which comprises administering to the substrate a bacterial composition with antagonistic activity against *Agrobacterium* biovar 1 for administration to plants, which comprises at least one isolated *Paenibacillus* strain or extract thereof wherein said at least one Paenibacillus strain comprises a 16S rRNA sequence with at least 93% sequence identity to the sequence of SEQ ID NO: 1.
38. The method of statement 37 wherein the at least one Paenibacillus strain comprises a 16S rRNA sequence with at least 95% sequence identity to the sequence of SEQ ID NO: 1.
39. The method of statements 37 or 38 wherein the at least one Paenibacillus strain comprises a 16S rRNA sequence with 100% sequence identity to the sequence of SEQ ID NO: 1.
40. The method according to any of the preceding statements, wherein the plant is a Tomato plant and the disease is Hairy Root Disease (HRD).
41. An isolated *Paenibacillus xylanexedens* strain deposited under accession number LMG P-29981.
42. An isolated *Paenibacillus xylanexedens* strain deposited under accession number LMG P-29983.
43. An isolated *Paenibacillus illinoisensis* strain deposited under accession number LMG P-29982.
44. An isolated *Paenibacillus illinoisensis* strain deposited under accession number LMG P-29984.
45. A composition comprising at least one of the isolated *Paenibacillus* strains according to any one of statements 41 to 44 or an extract of at least one of the isolated *Paenibacillus* strains according to any one of statements 41 to 44.
46. Plant seeds or seedlings coated or inoculated with at least one isolated *Paenibacillus* strain according to any one of statements 41 to 44 or with a composition according to statement 45.
47. An agricultural composition comprising at least one isolated *Paenibacillus* strain or an extract of at least one isolated *Paenibacillus* strain wherein said *Paenibacillus* strain comprises a 16S rRNA sequence with at least 93% sequence identity to the sequence of SEQ ID NO: 1.
48. The agricultural composition according to statement 47 wherein the at least one isolated *Paenibacillus* strain comprises a 16S rRNA sequence with at least 95% sequence identity to the sequence of SEQ ID NO: 1.
49. The agricultural composition according to statement 47 or 48 wherein the at least one isolated *Paenibacillus* strain comprises a 16S rRNA sequence with 100% sequence identity to the sequence of SEQ ID NO: 1.
50. The composition according to statement 45 or anyone of statements 47 to 49, wherein the composition is a substrate composition, a nutrient composition or a plant controller composition.
51. The composition according to statement 50, wherein the substrate composition is a hydroponics substrate composition.
52. The composition according to statement 51, wherein the hydroponics substrate composition comprises perlite, cocos, rockwool or a combination thereof.
53. Plant seeds or seedlings coated or inoculated with at least one isolated *Paenibacillus* strain or an extract of at least one *Paenibacillus* strain wherein said *Paenibacillus* strain comprises a 16S rRNA sequence with at least 93% sequence identity to the sequence of SEQ ID NO: 1.
54. The plant seeds or seedlings according to statement 53 wherein the at least one *Paenibacillus* strain comprises a 16S rRNA sequence with at least 95% sequence identity to the sequence of SEQ ID NO: 1.
55. The plant seeds or seedlings according to statement 53 or 54 wherein the at least one *Paenibacillus* strain comprises a 16S rRNA sequence with 100% sequence identity to the sequence of SEQ ID NO: 1.
56. The plant seeds or seedlings according to anyone of the statements 53 to 55, wherein the plant seeds or seedlings are tomato seeds or seedlings.
57. Use of at least one isolated *Paenibacillus* strain or an extract of at least one *Paenibacillus* strain, wherein said at least one *Paenibacillus* strain comprises a 16S rRNA sequence with at least 93% sequence identity to the sequence of SEQ ID NO: 1 for preventing or treating in a plant a rhizogenic or tumorigenic plant disease caused by bacteria in agriculture or horticulture.
58. The use according to statement 57, wherein the at least one *Paenibacillus* strain comprises a 16S rRNA sequence with at least 95% sequence identity to the sequence of SEQ ID NO: 1.
59. The use according to statement 57 or 58, wherein the at least one *Paenibacillus* strain comprises a 16S rRNA sequence with 100% sequence identity to the sequence of SEQ ID NO: 1.
60. The use according to anyone of statements 57 to 59, wherein the rhizogenic or tumorigenic plant disease is caused by Agrobacteria or Rhizobia bacteria; in particular caused by Agrobacteria biovar 2 strains or Rhizobia vitis strains.
61. The use according to anyone of statements 57 to 60, wherein the rhizogenic plant disease is hairy root disease (HRD).
62. The use according to anyone of statements 57 to 60 wherein the tumorigenic plant disease is crown gall disease.
63. The use according to any one of the statements 57 to 62, wherein the at least one *Paenibacillus* strain is selected from the group consisting of *Paenibacillus xylanexedens* having collection number DSM15478, *Paenibacillus illinoisensis* having collection number DSM11733, *Paenibacillus pabuli* having collection number LMG15970, *Paenibacillu xylanexedens* having collection number LMG P-29983, *Paenibacillus illinoisensis* having collection number LMG P-29984, *Paenibacillus illinoisensis* having collection number LMG P-29982, *Paenibacillus xylanexedens* having collection number LMG P-29981, *Paenibacillus taichungensis* having collection number DSM19942, *Paenibacillus tundrae* having collection number DSM21291, *Paenibacillus tylopili* having collection number DSM18927 and *Paenibacillus xylanilyticus* having collection number DSM17255; or a derivative, variant or mutant of any thereof.
64. The use according to statement 63, wherein the at least one *Paenibacillus* strain is selected from *Paenibacillus xylanexedens* having collection number LMG P-29981, *Paenibacillus xylanexedens* having collection number LMG P-29983, *Paenibacillus illinoisensis* having collection number LMG P-29982, or *Paenibacillus illinoisensis* having collection number LMG P-29984.
65. The use according to statement 64, wherein the at least one *Paenibacillus* strain is selected from *Paenibacillus xylanexedens* having collection number LMG P-29981 or *Paenibacillus xylanexedens* having collection number LMG P-29983.
66. The use according to any of the statements 57 to 65, wherein the plant is a crop plant.
67. The use according to statement 66, wherein the crop plant is selected from the group consisting of eggplant, cucumber plant and tomato plant.

68. The use according to statement 67, wherein the crop plant is a tomato plant.
69. The use according to anyone of the statements 57 to 68, wherein the plant is grown on a tomato rootstock.
70. The use according to anyone of the statements 57 to 69, wherein the at least one *Paenibacillus* strain or extract of at least one *Paenibacillus* strain is administered to the plant by a method selected from the group consisting of: applying directly onto the substrate on which seedlings are grown, adding to the irrigation water, applying to the hydroponics substrate, application to seed, and foliar spraying.
71. A method of identifying a *Paenibacillus* strain with activity against bacteria causing rhizogenic or tumorigenic plant diseases, said method comprising the following steps:
    providing a *Paenibacillus* strain,
    sequencing the 16S rRNA sequence of said *Paenibacillus* strain and determining therein a sequence with at least 93% identity to the sequence of SEQ ID NO: 1.
    identifying the *Paenibacillus* strain comprising a 16S rRNA sequence with at least 93% identity to the sequence of SEQ ID NO: 1 as a *Paenibacillus* strain with activity against bacteria causing rhizogenic or tumorigenic plant diseases.
72. The method according to statement 71 further comprising the step of applying the identified *Paenibacillus* strain on a plant with a rhizogenic or tumorigenic plant disease and determining the activity of said *Paenibacillus* strain.
73. The method according to statement 71 further comprising applying the identified *Paenibacillus* strain on a plant that is susceptible to a rhizogenic or tumorigenic plant disease and determining the activity of said *Paenibacillus* strain in preventing said rhizogenic or tumorigenic plant disease.
74. The method according to anyone of the statements 71 to 73 wherein a sequence with at least 95% identity to the sequence of SEQ ID NO: 1 is determined and wherein the *Paenibacillus* strain comprising a 16S rRNA sequence with said sequence is identified as a *Paenibacillus* strain with activity against bacteria causing rhizogenic or tumorigenic plant disease.
75. The method according to anyone of the statements 71 to 74 wherein a sequence with 100% sequence identity to the sequence of SEQ ID NO: 1 is determined and wherein the *Paenibacillus* strain comprising a 16S rRNA sequence with said sequence is identified as a *Paenibacillus* strain with activity against bacteria causing rhizogenic or tumorigenic plant diseases.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE PREFERRED EMBODIMENTS

Figure 1:
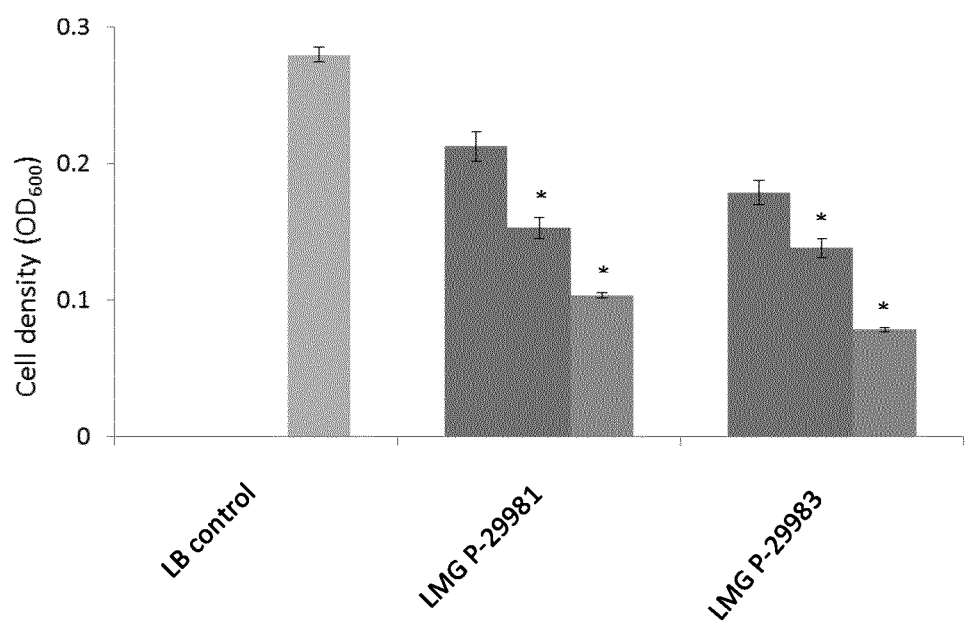
FIG. 1. Antagonistic activity of cell-free culture filtrates (CF) of selected *Paenibacillus* isolates (LMG P-29981 and LMG P-29983) against rhizogenic *Agrobacterium* biovar 1 (isolate ST15.13/097). *Paenibacillus* cultures of $10^4$ cells per mL were filter-sterilized and 100 (left bar), 150 (middle bar) and 190 µL (right bar) of the cell-free filtrates were added to 100, 50 and 10 µL *Agrobacterium*-containing LB (final concentration of $5 \times 10^2$ cells per mL), respectively. Plates were photospectrometrically (OD600) read after 24 h. Presented data are means of two independent experiments (2 replicates per experiment) and error bars represent standard error of the mean. The asterisk indicates a statistically significant difference (Student t-test) with the control (P<0.05).

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but do not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

In this study, the effects of various bacterial strains, were evaluated for improvements in health and growth of the plants. The bacterial strains or extracts thereof improve plant defenses against disease, with the effect of increasing the health and growth of plants. Therefore, this approach can be used to treat, for example, plants that are susceptible to infection with, or plants that exhibit symptoms of HRD disease or infection with a rhizogenic *Agrobacterium* species.

Examples of such species include *Agrobacterium* biovar 1.

While a number of embodiments of the present invention have been shown and described herein in the present context, such embodiments are provided by way of example only, and not of limitation. Numerous variations, changes and substitutions will occur to those of skill in the art without materially departing from the invention herein. Any means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

All technical and scientific terms used herein, unless defined herein, are intended to have the same meaning as commonly understood by one of ordinary skill in the art. The techniques employed herein are also those that are known to one of ordinary skill in the art, unless stated otherwise.

The term "applying," "application," "administering," "administration," and all their cognates, as used herein, refers to any method for contacting the plant with the bacteria and bacterial compositions discussed herein. Administration generally is achieved by application of the bacteria, in a vehicle compatible with the plant to be treated (i.e., a botanically compatible vehicle or carrier), such as an aqueous vehicle, to the plant, to the soil or hydroponic substrate surrounding the plant. Any application means can be used, however preferred application is to the hydroponic substrate surrounding the plant, so that the applied bacteria preferably come into contact with the plant roots and can colonize the roots. However, the bacteria can also be added to the irrigation water in the desired concentration to disperse the bacteria through the irrigation system and the hydroponics substrate. This allows for automated and continuous dosing, which may result in an even higher effectiveness of the bacteria. Alternatively, the bacteria can be applied to the hydroponics substrate before planting the tomato seedlings. During the production system of the hydroponics substrate, the bacteria can be mixed with perlite, cocos, rockwool, which is used to produce the hydroponics substrate. Finally, the bacteria can be used to coat tomato seed, thereby protecting the young seedlings.

The term "bacteria," as used herein, refers to any prokaryotic microorganism, and is intended to include both Gram positive and Gram negative bacteria, and unclassified bacteria. The term "beneficial bacteria," as used herein, refers to the bacteria of strains *Paenibacillus xylanexedens* DSM15478, *Paenibacillus illinoisensis* DSM11733, *Paenibacillus pabuli* LMG15970, *Paenibacillus xylanexedens* LMG P-29983, *Paenibacillus illinoisensis* LMG P-29984, *Paenibacillus illinoisensis* LMG P-29982, *Paenibacillus xylanexedens* LMG P-29981, *Paenibacillus taichungensis* DSM19942, *Paenibacillus tundrae* DSM21291, *Paenibacillus tylopili* DSM18927 and *Paenibacillus xylanilyticus* DSM17255, described herein and deposited in accordance with the requirements of the Budapest Treaty. Further, strains that have at least 99% identity to the 16s rRNA of these deposited strains or alternatively strains of which the 16S rRNA comprises a sequence with at least 93% sequence identity to the sequence of SEQ ID NO: 1 (ttgggacaac taccggaaac ggtagctaat accgaata) are considered "genetic equivalents" of the specific deposited strains. In embodiments described and/or claimed herein, genetic equivalents may be used as an alternative in place of beneficial bacteria.

The term "extract" refers to any aqueous extract from any of the beneficial bacteria according to the present invention obtained after lysis of the cells, as well as the supernatant obtained from culturing these beneficial bacteria under liquid fermentation conditions. Lysates of the cells and of the medium may be further fractionated or purified, and optionally reformulated in an different aqueous solution.

The term "botanically acceptable carrier/vehicle" or "botanically compatible carrier/vehicle," as used herein, refers to any non-naturally occurring vehicle, in liquid, solid or gaseous form which is compatible with use on a living plant and is convenient to contain a substance or substances for application of the substance or substances to the plant, its leaves or root system, its seeds, the soil surrounding the plant, or for injection into the trunk, or any known method of application of a compound to a living plant, preferably a crop plant, for example a eggplant, cucumber plant or tomato plant. Useful vehicles can include any known in the art, for example liquid vehicles, including aqueous vehicles, such as water, solid vehicles such as powders, granules or dusts, or gaseous vehicles such as air or vapor. Any vehicle which can be used with known devices for soaking, drenching, injecting into the soil or hydroponic substrate surrounding the plant, spraying, dusting, or any known method for applying a compound to a plant, is contemplated for use with embodiments of the invention. Typical carriers and vehicles contain inert ingredients such as fillers, bulking agents, buffers, preservatives, anti-caking agents, pH modifiers, surfactants, soil wetting agents, adjuvants, and the like.

Suitable carriers and vehicles within this definition also can contain additional active ingredients such as plant defense inducer compounds, nutritional elements, fertilizers, pesticides, and the like. In a particular embodiment, the botanically acceptable vehicle pertains to a vehicle component, or vehicle formulation, that is not found in nature. In another embodiment, the botanically acceptable vehicle may pertain to a vehicle found in nature, but where the vehicle and the bacteria strain(s) are not mixed or combined together in nature.

The term "Tomato" or "tomato," as used herein, refers to any plant of the species *Solanum lycopersicum* family Solanaceae and includes the tomato cultivars 'Kanavaro', 'Admiro', 'Rebelski', 'Merlice', 'Foundation', 'Prunus', and 'Brioso', and rootstocks Maxifort and DR0141TX.

The term "crop plant," as used herein, includes any cultivated plant grown for food, feed, fiber, biofuel, medicine, or other uses. Such plants include, but are not limited to, eggplant, citrus, corn, cucumber, soybean, tomato, sugar cane, strawberry, wheat, rice, cassava, potato, cotton, and the like. The term "crop," as used herein, refers to any of the food (including fruits or juice), feed, fiber, biofuel, or medicine derived from a crop plant. All crop plants are contemplated for use with the invention, including monocots and dicots.

The term "effective amount" or "therapeutically effective amount," as used herein, means any amount of the bacterial strain, combination of bacterial strains or composition containing the bacterial strains or extract thereof, which improves health, growth or productivity of the plant, or which reduces the effects, titer or symptoms of the plant disease, or prevents worsening of the plant disease, symptoms or infection of the plant. This term includes an amount effective to increase seed germination of a plant or a plant population, to increase the speed of seed germination of a plant or a plant population, to increase growth rates of a plant or a plant population, to increase crop yield of a plant or plant population, increase crop quality in a plant or plant population, reduce the plant pathogen titer, to inhibit plant pathogen growth, to reduce the percent of infected plants in a plant population, to reduce the percent of plants showing disease symptoms in a plant or plant population, to reduce the disease symptom severity rating or damage rating of a plant or plant population, to reduce average pathogen population or titer in a plant or plant population by about 2%, about 5%, about 10%, about 20%, about 30%, about 40%, about 50%, about 60%, about 70%, about 75%, about 80%, about 85%, about 90%, or more, compared to plants or a plant population not treated with the active ingredient.

The term "faster growth," as used herein, refers to a measurable increase in the rate of growth of a plant, including seedlings, stems, roots, seeds, flowers, fruits, leaves and shoots thereof.

The term "health," as used herein, refers to the absence of illness and a state of well-being and fitness, and refers to the level of functional or metabolic efficiency of the plant, including the ability to adapt to conditions and to combat disease, while maintaining growth and development. The term "vigor," as used herein, refers to the health, vitality and hardiness of a plant, and its capacity for natural growth and survival. Therefore, the phrase "health and vigor of a plant," as used herein, means the absence of illness, a high level of functional or metabolic efficiency, the ability to combat disease, and the maintenance of good growth and development, and the efficient production of crops.

The term "healthy," as used herein, refers to a plant or plant population which is not known currently to be affected by a plant disease.

"Tumorigenic and rhizogenic plant diseases" are a group of plant diseases resulting in excessive plant tissue formation. The symptoms are caused by the insertion of a small segment of T-DNA 'transfer DNA', which is transferred from bacteria to plants.

The term "Hairy root disease," as used herein, is a disease of plants caused by microorganisms of the *Agrobacterium rhizogenes*, such as *Agrobacterium* biovar 1 or biovar 2. This disease, for example, can be found in tomato plants, or other plants in the genus *Solanum*. Biovar 2 is particularly relevant in the development of Hairy root disease in Rosaceae. Hairy root disease induces the formation of proliferative multi-branched adventitious roots at the site of infection; so-called 'hairy roots'. Symptoms include overdevelopment of a root system that is not completely geotropic. In severe cases, substantial losses in marketable yield are observed.

The term "Crown gall," as used herein refers to a disease of plants caused by the bacterium *Rhizobium vitis*, which enters the plant through wounds in roots or stems and stimulates the plant tissues to grow in a disorganized way, producing swollen galls. This disease can be found in grape vine.

The term "treating" or "treatment," or its cognates, as used herein refers to any application or administration to a plant, the soil surrounding the plant or the hydroponics substrate, the water applied to the plant, or the hydroponic system in which the plant is grown, which is intended to improve the health, growth or productivity of a plant, particularly a crop plant and includes any process or method which cures, diminishes, ameliorates, or slows the progress of the disease or disease symptoms. Thus, treatment includes reducing bacterial titer in plant tissues, hydroponics substrate or plant rhizosphere, or appearance of disease symptoms relative to controls which have not undergone treatment. For example, a treatment intended to increase the health or growth or a crop plant, increase crop yield of a plant or population of plants is contemplated as part of this definition, as well as treatment intended to improve disease symptoms or pathogen titer in the plant.

The term "improved ability to defend against disease," as used herein, refers to a measurable increase in plant defense against a disease. This can be measured in terms of a measurable decrease in disease symptoms, pathogen titer, or loss of crop yield and/or quality, or a measurable increase in growth, crop quantity or quality.

The term "improved crop productivity," as used herein, refers to a measurable increase in the quantity of a crop in a plant or a population of plants, in terms of numbers, size, or weight of crop seeds, fruits, vegetable matter, fiber, grain, and the like.

The term "improved crop quality," as used herein, refers to a measurable increase in the quality of a crop, in terms of numbers, size, or weight of crop seeds, fruits, vegetable matter, fiber, grain, and the like, or in terms of sugar content, juice content, unblemished appearance, color, and/or taste.

The term "improved resistance to disease," as used herein, refers to an increase of plant defense in a healthy plant or a decrease in disease severity in a plant or in a population of plants, or in the number of diseased plants in a plant population. The term "improved seed germination," as used herein, means a measurable increase of the chance of successful germination of an individual seed, a measurable increase in the percentage of seeds successfully germinating, and/or a measurable increase in the speed of germination.

The term "improved seedling emergence," as used herein means a measurable increase in the speed of growth and/or development of successfully germinated individual seeds or population of seeds.

The term "measurable increase" (or "measurable decrease"), as used herein, means an increase (or decrease) that can be detected by assays known in the art as greater (or less) than control. For example, a measurable increase (or decrease) is an increase (or decrease) of about 2%, about 5%, about 10%, about 20%, about 30%, about 40%, about 50%, about 60%, about 70%, about 75%, about 80%, about 85%, about 90%, or more, compared to plants or a plant population not treated with the active ingredient.

The term "plant in need thereof," as used herein, means any plant which is healthy or which has been diagnosed with a plant disease or symptoms thereof, or which is susceptible to a plant disease, or may be exposed to a plant disease or carrier thereof.

The term "plant disease," as used herein, refers to any disease of a crop plant, caused by any plant pathogen, including but not limited to, bacterial, viral, fungal nematode, phytomyxean, protozoan, algal and parasite plant pathogens.

The term "plant disease symptoms," as used herein, refers to any symptom of disease, including the detectable presence of a known plant pathogen, or the presence of rot, mottling, galls, discoloration such as yellowing or browning, fruit greening, stunted growth, plant death, cellular death, cell wall breakdown, and/or the presence of spots, lesions, dieback, wilting, dwarfing, Witch's broom and/or knots, or the presence of excessive root development.

The term "population of plants," as used herein, refers to a group of plants, all of the same species, that inhabit a particular area at the same time. Therefore, the plants in a nursery, a grove, a farm, and the like are considered a population.

The term "reduction of disease symptoms," as used herein, refers to a measurable decrease in the number or severity of disease symptoms.

The present application provides a new method for pest and disease control technology with less environmental impact than chemical pesticides, and relates more in particular to the use of biocontrol organisms for improving the health and vigor of plants. The method comprises administering to the plant an effective amount of at least one isolated bacterial strain with antagonistic activity against *Agrobacterium* biovar 1 or extract thereof of which the 16S rRNA comprises a sequence with at least 80%, preferably at least 85%, more preferably at least 93%, most preferably 95% sequence identity to the sequence of SEQ ID No 1, wherein the improvement in health and vigor is one or more of improved resistance to disease; improved ability to defend against disease; reduction of disease symptoms; improved crop productivity.

The biocontrol organisms envisaged herein are selected from the group consisting of *Paenibacillus xylanexedens* having collection number DSM15478, *Paenibacillus illinoisensis* having collection number DSM11733, *Paenibacillus pabuli* having collection number LMG15970, *Paenibacillus xylanexedens* having collection number LMG P-29983, *Paenibacillus illinoisensis* having collection number LMG P-29984, *Paenibacillus illinoisensis* having collection number LMG P-29982, *Paenibacillus xylanexedens* having collection number LMG P-29981, *Paenibacillus taichungensis* having collection number DSM19942, *Paenibacillus tundrae* having collection number DSM21291, *Paenibacillus tylopili* having collection number DSM18927 and *Paenibacillus xylanilyticus* having collection number DSM17255 or a derivative, variant or mutant of any thereof. In an even preferred embodiment, the biocontrol organisms envisaged herein are selected from the group consisting of *Paenibacillus* having collection number LMG P-29981 and *Paenibacillus xylanexedens* having collection number LMG P-29983.

The studies described herein have shown that the bacterial cultures according to embodiments of the invention have desirable effects on the growth of plants, their productivity and their ability to combat disease. The invention is contemplated for use on plants at all stages of development, including seeds, seedlings and mature plants, which are cultivated by any method known in the art which is convenient for the plant in question. The plants envisaged to be used in the invention are crop plants, more particularly a crop selected from the group consisting of Rosaceae, grape vine, eggplant, cucumber and tomato, or a crop grown on a tomato rootstock, preferably from the group consisting of eggplant, cucumber and tomato. In a preferred embodiment the plant is a tomato plant. In a more preferred embodiment the plant is the tomato cultivar 'Rebelski', or a plant grown on the rootstock Maxifort.

The plant can be healthy or affected by a plant disease or plant disease symptoms. In particular embodiments, the plant is affected by a bacterial disease, more specifically a rhizogenic or tumorigenic plant disease caused by bacteria, even more specifically a rhizogenic or tumorigenic plant diseases caused by Agrobacteria or Rhizobia bacteria; even more specifically, a rhizogenic or tumorigenic plant disease caused by Agrobacteria biovar 2 strains or Rhizobia vitis strains. In a more particular embodiment the disease is Hairy Root Disease (HRD) or crown gall disease. In a preferred embodiment, the disease is HRD in eggplant, cucumber plant or tomato plant.

Prevention of a rhizogenic or tumorigenic plant disease can be understood as a reduction in the incidence infection with a bacterial disease after exposure of the plants to the corresponding bacteria. The reduction rate can vary between 10% and 100%, in particular between 30% and 100%.

Persons of skill are aware of various methods to apply compounds, including live bacteria, to plants for surface application or for uptake, and any of these methods are contemplated for use in this invention. Methods of administration to plants include, by way of non-limiting example, application to any part of the plant, by inclusion in irrigation water, by injection to the plant or to the soil or substrate surrounding the plant, or by exposure of the root system to aqueous solutions containing the compounds, by use in hydroponic or aeroponic systems, by seed treatment, by application to the roots, stems or leaves, by application to the plant interior, or any part of the plant to be treated. Any means known to those of skill in the art is contemplated. Application of the bacteria can be performed in a nursery setting, a greenhouse, hydroponics facility, or in the field, or any setting where it is desirable to treat plants which have been or can become exposed to a plant disease, such as HRD, or which can benefit from an enhancement of health and vigor. The methods and bacteria of this invention can be used to treat infection with a plant pathogen and can be used to improve plant defenses or health, growth and productivity in plants which are not infected. Thus, any plant in need, in the context of this invention, includes any plant susceptible to a lack of optimum health and vigor, or susceptible to a plant disease, whether currently infected or in potential danger of infection, in the judgement of the person of skill in this and related arts.

Any method of administering the bacteria which brings the bacteria in contact with the roots of the plant is preferred. The concentrations, volumes, and duration may change depending on the plant and can be determined by one of skill in the art, however preferred methods are those wherein the administering to the plant provides at least a concentration between $10^2$ and $10^{12}$ cfu, preferably $10^8$ cfu of the bacterial strain per plant. A preferred goal of the administration of the bacteria according to embodiments of the invention is to increase the colony-forming units of the bacterial strains at the roots of the plants, and particularly to increase those levels above any natural levels, if any. Therefore compositions are administered to deliver an amount of bacteria to achieve this goal.

Compositions according to embodiments of the invention preferably include a botanically acceptable vehicle or carrier, preferably a liquid, aqueous vehicle or carrier such as water, and at least one bacterial strain. The composition may be formulated as an emulsifiable concentrate(s), suspension concentrate(s), directly sprayable or dilutable solution(s), coatable paste(s), dilute emulsion(s), wettable powder(s), soluble powder(s), dispersible powder(s), dust(s), granule(s) or capsule(s).

The composition may optionally include a botanically acceptable carrier that contains or is blended with additional active ingredients and/or additional inert ingredients. Active ingredients which can be included in the carrier formulation can be selected from any combination of pesticides, herbicides, plant nutritional compositions such as fertilizers, and the like. Plant inducer compounds such as salicylic acid or β-aminobutyric acid (BABA) also can be included in the compositions. Additional active ingredients can be administered simultaneously with the bacterial strains described here, in the same composition, or in separate compositions, or can be administered sequentially.

Inert ingredients which can be included in the carrier formulation can be selected from any compounds to aid in the physical or chemical properties of the composition. Such inert ingredients can be selected from buffers, salts, ions bulking agents, colorants, pigments, dyes, fillers, wetting agents, dispersants, emulsifiers, penetrants, preservatives, antifreezes, evaporation inhibitors, bacterial nutrient compounds, anti-caking agents, defoamers, antioxidants, and the like.

In certain embodiments the present invention is used as a method of enhancing growth of a plant. In other embodiments it is used as a method of prevention of a plant disease in a plant in need thereof, which comprises administering to the substrate a bacterial composition with antagonistic activity against *Agrobacterium* biovar 1 or biovar 2 for administration to plants, which comprises at least one isolated bacterial strain or extract thereof of which the 16S rRNA comprises a sequence with at least 90% sequence identity to the sequence of SEQ ID No (ttgggacaac taccggaaac ggtagctaat accgaata). Preferably, the plant a Tomato plant and the disease is Hairy Root Disease (HRD).

Other embodiments, objects, features and advantages will be set forth in the examples that follow. The summary above is to be considered as a brief and general overview of some of the embodiments disclosed herein, is provided solely for the benefit and convenience of the reader, and is not intended to limit in any manner the scope encompassed by the appended claims.

EXAMPLES

Example 1. Experimental Methods

Culture Collection and Screening for Antagonists of Rhizogenic Agrobacteria

In a first screening, a collection of 130 phylogenetically different bacterial strains isolated from soil habitats (De Ridder-Duine, A. S. et al. (2005) *Soil Biol. Biochem.* 37, 349-357) was used in this study and subjected to high-throughput screening for candidate BCO of rhizogenic agrobacteria as described previously (Tyc, O. et al. (2014) *Front Microbiol* 5, 567) (Table 1).

TABLE 1

Detailed results of antagonistic activity screening of 130 bacterial isolates[a] against rhizogenic *Agrobacterium* biovar 1 (isolate ST15.13/097)[b].

| Phylum/Class | Taxonomic affiliation[c] | GenBank Accession number 16S rRNA gene | Growth inhibition |
|---|---|---|---|
| Actinobacteria | | | |
| Actinobacteria | *Microbacterium* sp. AD141 | KJ685346 | – |
| Actinobacteria | *Micrococcus* sp. AD31 | KJ685246 | – |
| Actinobacteria | *Rhodococcus* sp. AD22 | KJ685237 | – |
| Actinobacteria | *Streptomyces* sp. AD107 | KJ685318 | – |
| Actinobacteria | *Streptomyces* sp. AD108 | KJ685319 | – |
| Actinobacteria | *Streptomyces* sp. AD29 | KJ685244 | – |
| Actinobacteria | *Streptomyces* sp. AD92 | KJ685303 | – |
| Actinobacteria | *Streptomyces* sp. AD94 | KJ685305 | – |
| Actinobacteria | *Tsukamurella* sp. AD106 | KJ685317 | – |
| Bacteroidetes | | | |
| Flavobacteria | *Chryseobacterium* sp. AD48 | KJ685263 | – |
| Flavobacteria | *Flavobacterium* sp. AD43 | KJ685258 | – |
| Flavobacteria | *Flavobacterium* sp. AD131 | KJ685338 | – |
| Flavobacteria | *Flavobacterium* sp. AD134 | KJ685341 | – |
| Flavobacteria | *Flavobacterium* sp. AD142 | KJ685347 | – |
| Flavobacteria | *Flavobacterium* sp. AD146 | KJ685351 | – |
| Flavobacteria | *Flavobacterium* sp. AD155 | KJ685358 | – |
| Flavobacteria | *Flavobacterium* sp. AD156 | KJ685359 | – |
| Flavobacteria | *Flavobacterium* sp. AD41 | KJ685256 | – |
| Flavobacteria | *Flavobacterium* sp. AD42 | KJ685257 | – |

TABLE 1-continued

Detailed results of antagonistic activity screening of 130 bacterial isolates[a] against rhizogenic *Agrobacterium* biovar 1 (isolate ST15.13/097)[b].

| Phylum/Class | Taxonomic affiliation[c] | GenBank Accession number 16S rRNA gene | Growth inhibition |
|---|---|---|---|
| Flavobacteria | *Flavobacterium* sp. AD44 | KJ685259 | − |
| Flavobacteria | *Flavobacterium* sp. AD45 | KJ685260 | − |
| Flavobacteria | *Flavobacterium* sp. AD84 | KJ685296 | − |
| Flavobacteria | *Flavobacterium* sp. AD86 | KJ685298 | − |
| Flavobacteria | *Flavobacterium* sp. AD91 | KJ685302 | − |
| Sphingobacteria | *Pedobacter* sp. V48 | DQ778037 | − |
| Firmicutes | | | |
| Bacilli | *Bacillus* sp. AD78 | KJ685290 | − |
| Bacilli | *Paenibacillus* sp. AD116 | KJ685325 | − |
| Bacilli | *Paenibacillus* sp. LMG P-29981 | KJ685326 | + |
| Bacilli | *Paenibacillus* sp. AD50 | KJ685264 | − |
| Bacilli | *Paenibacillus* sp. AD83 | KJ685295 | − |
| Bacilli | *Paenibacillus* sp. AD87 | KJ685299 | − |
| Bacilli | *Paenibacillus* sp. AD93 | KJ685304 | − |
| Proteobacteria | | | |
| Alpha-proteobacteria | *Agrobacterium* sp. AD1 | KJ685218 | − |
| Alpha-proteobacteria | *Agrobacterium* sp. AD140 | KJ685345 | − |
| Alpha-proteobacteria | *Bosea* sp. AD113 | KJ685323 | − |
| Alpha-proteobacteria | *Bosea* sp. AD132 | KJ685339 | − |
| Alpha-proteobacteria | *Bradyrhizobiaceae* sp. AD126 | KJ685334 | − |
| Alpha-proteobacteria | *Mesorhizobium* sp. AD112 | KJ685322 | − |
| Alpha-proteobacteria | *Phyllobacterium* sp. AD136 | KJ685342 | − |
| Alpha-proteobacteria | *Phyllobacterium* sp. AD152 | KJ685356 | − |
| Alpha-proteobacteria | *Phyllobacterium* sp. AD153 | KJ685357 | − |
| Alpha-proteobacteria | *Phyllobacterium* sp. AD159 | KJ685361 | − |
| Alpha-proteobacteria | *Phyllobacterium* sp. AD34 | KJ685249 | − |
| Alpha-proteobacteria | *Phyllobacterium* sp. AD51 | KJ685265 | − |
| Beta-proteobacteria | *Burkholderia* sp. AD10 | KJ685227 | − |
| Beta-proteobacteria | *Burkholderia* sp. AD11 | KJ685228 | − |
| Beta-proteobacteria | *Burkholderia* sp. AD123 | KJ685331 | − |
| Beta-proteobacteria | *Burkholderia* sp. AD127 | KJ685335 | − |
| Beta-proteobacteria | *Burkholderia* sp. AD138 | KJ685344 | − |
| Beta-proteobacteria | *Burkholderia* sp. AD15 | KJ685231 | − |
| Beta-proteobacteria | *Burkholderia* sp. AD18 | KJ685234 | − |
| Beta-proteobacteria | *Burkholderia* sp. AD24 | KJ685239 | − |
| Beta-proteobacteria | *Burkholderia* sp. AD25 | KJ685240 | − |
| Beta-proteobacteria | *Burkholderia* sp. AD26 | KJ685241 | − |
| Beta-proteobacteria | *Burkholderia* sp. AD27 | KJ685242 | − |
| Beta-proteobacteria | *Burkholderia* sp. AD28 | KJ685243 | − |
| Beta-proteobacteria | *Burkholderia* sp. AD30 | KJ685245 | − |
| Beta-proteobacteria | *Burkholderia* sp. AD32 | KJ685247 | − |
| Beta-proteobacteria | *Burkholderia* sp. AD35 | KJ685250 | − |
| Beta-proteobacteria | *Burkholderia* sp. AD37 | KJ685252 | − |
| Beta-proteobacteria | *Burkholderia* sp. AD9 | KJ685226 | − |
| Beta-proteobacteria | *Collimonas* sp. AD137 | KJ685343 | − |
| Beta-proteobacteria | *Collimonas* sp. AD101 | KJ685312 | − |
| Beta-proteobacteria | *Collimonas* sp. AD102 | KJ685313 | − |
| Beta-proteobacteria | *Collimonas* sp. AD103 | KJ685314 | − |
| Beta-proteobacteria | *Collimonas* sp. AD19 | KJ685235 | − |
| Beta-proteobacteria | *Collimonas* sp. AD23 | KJ685238 | − |
| Beta-proteobacteria | *Collimonas* sp. AD33 | KJ685248 | − |
| Beta-proteobacteria | *Collimonas* sp. AD58 | KJ685270 | − |
| Beta-proteobacteria | *Collimonas* sp. AD59 | KJ685271 | − |
| Beta-proteobacteria | *Collimonas* sp. AD60 | KJ685272 | − |
| Beta-proteobacteria | *Collimonas* sp. AD61 | KJ685273 | − |
| Beta-proteobacteria | *Collimonas* sp. AD62 | KJ685274 | − |
| Beta-proteobacteria | *Collimonas* sp. AD63 | KJ685275 | − |
| Beta-proteobacteria | *Collimonas* sp. AD64 | KJ685276 | − |
| Beta-proteobacteria | *Collimonas* sp. AD65 | KJ685277 | − |
| Beta-proteobacteria | *Collimonas* sp. AD66 | KJ685278 | − |
| Beta-proteobacteria | *Collimonas* sp. AD67 | KJ685279 | − |
| Beta-proteobacteria | *Collimonas* sp. AD68 | KJ685280 | − |
| Beta-proteobacteria | *Collimonas* sp. AD69 | KJ685281 | − |
| Beta-proteobacteria | *Collimonas* sp. AD70 | KJ685282 | − |
| Beta-proteobacteria | *Collimonas* sp. AD71 | KJ685283 | − |
| Beta-proteobacteria | *Collimonas* sp. AD76 | KJ685288 | − |
| Beta-proteobacteria | *Collimonas* sp. AD77 | KJ685289 | − |

TABLE 1-continued

Detailed results of antagonistic activity screening of 130 bacterial isolates[a] against rhizogenic *Agrobacterium* biovar 1 (isolate ST15.13/097)[b].

| Phylum/Class | Taxonomic affiliation[c] | GenBank Accession number 16S rRNA gene | Growth inhibition |
|---|---|---|---|
| Beta-proteobacteria | *Collimonas* sp. AD88 | KJ685300 | – |
| Beta-proteobacteria | *Collimonas* sp. AD89 | KJ685301 | – |
| Beta-proteobacteria | *Collimonas* sp. AD95 | KJ685306 | – |
| Beta-proteobacteria | *Collimonas* sp. AD98 | KJ685309 | – |
| Beta-proteobacteria | *Collimonas* sp. AD99 | KJ685310 | – |
| Beta-proteobacteria | *Janthinobacterium* sp. AD144 | KJ685349 | – |
| Beta-proteobacteria | *Janthinobacterium* sp. AD54 | KJ685267 | – |
| Beta-proteobacteria | *Janthinobacterium* sp. AD55 | KJ685268 | – |
| Beta-proteobacteria | *Janthinobacterium* sp. AD72 | KJ685284 | – |
| Beta-proteobacteria | *Janthinobacterium* sp. AD73 | KJ685285 | – |
| Beta-proteobacteria | *Janthinobacterium* sp. AD74 | KJ685286 | – |
| Beta-proteobacteria | *Janthinobacterium* sp. AD75 | KJ685287 | – |
| Beta-proteobacteria | *Janthinobacterium* sp. AD80 | KJ685292 | – |
| Beta-proteobacteria | *Janthinobacterium* sp. AD96 | KJ685307 | – |
| Beta-proteobacteria | *Roseateles* sp. AD145 | KJ685350 | – |
| Beta-proteobacteria | *Silvimonas* sp. AD81 | KJ685293 | – |
| Beta-proteobacteria | *Silvimonas* sp. AD82 | KJ685294 | – |
| Beta-proteobacteria | *Variovorax* sp. AD130 | KJ685337 | – |
| Beta-proteobacteria | *Variovorax* sp. AD133 | KJ685340 | – |
| Beta-proteobacteria | *Variovorax* sp. AD143 | KJ685348 | – |
| Beta-proteobacteria | *Variovorax* sp. AD39 | KJ685254 | – |
| Gamma-proteobacteria | *Dyella* sp. AD129 | KJ685336 | – |
| Gamma-proteobacteria | *Dyella* sp. AD46 | KJ685261 | – |
| Gamma-proteobacteria | *Frateuria* sp. AD120 | KJ685329 | – |
| Gamma-proteobacteria | *Luteibactor* sp. AD20 | KJ685236 | – |
| Gamma-proteobacteria | *Lysobacter* sp. AD52 | KJ685266 | – |
| Gamma-proteobacteria | *Pseudomonas* sp. AD6 | KJ685223 | – |
| Gamma-proteobacteria | *Pseudomonas* sp. AD122 | KJ685330 | – |
| Gamma-proteobacteria | *Pseudomonas* sp. AD100 | KJ685311 | – |
| Gamma-proteobacteria | *Pseudomonas* sp. AD104 | KJ685315 | – |
| Gamma-proteobacteria | *Pseudomonas* sp. AD105 | KJ685316 | – |
| Gamma-proteobacteria | *Pseudomonas* sp. AD114 | KJ685324 | – |
| Gamma-proteobacteria | *Pseudomonas* sp. AD124 | KJ685332 | – |
| Gamma-proteobacteria | *Pseudomonas* sp. AD125 | KJ685333 | – |
| Gamma-proteobacteria | *Pseudomonas* sp. AD14 | KJ685230 | – |
| Gamma-proteobacteria | *Pseudomonas* sp. AD157 | KJ685360 | – |
| Gamma-proteobacteria | *Pseudomonas* sp. AD16 | KJ685232 | – |
| Gamma-proteobacteria | *Pseudomonas* sp. AD17 | KJ685233 | – |
| Gamma-proteobacteria | *Pseudomonas* sp. AD21 | DQ778036 | – |
| Gamma-proteobacteria | *Pseudomonas* sp. AD36 | KJ685251 | – |
| Gamma-proteobacteria | *Pseudomonas* sp. AD4 | KJ685221 | – |
| Gamma-proteobacteria | *Pseudomonas* sp. AD5 | KJ685222 | – |
| Gamma-proteobacteria | *Pseudomonas* sp. AD79 | KJ685291 | – |
| Gamma-proteobacteria | *Pseudomonas* sp. AD8 | KJ685225 | – |
| Gamma-proteobacteria | *Rhodonobacter* sp. AD109 *Stenotrophomonas* sp. | KJ685320 | – |
| Gamma-proteobacteria | AD147 | KJ685352 | – |

[a]The collection consisted of 130 isolates from soil habitats (de Ridder-Duine et al., 2005, cited above) and has previously been evaluated for antagonistic activity against *Escherichia coli* and *Staphylococcus aureus* (Tyc et al., 2014, cited above).
[b]Antagonistic activity was evaluated using the agar overlay assay (Bosmans et al., 2016b cited above). The strain with antagonistic activity produced a clear zone of inhibition where *Agrobacterium* growth was inhibited.
[c]Identifications based on16S rRNA gene analysis.

The collection consisted of isolates from different phyla and different classes (Table 2), and has previously been evaluated for antagonistic activity against two human pathogenic model organisms, including *Escherichia coli* and *Staphylococcus aureus* (Tyc et al., 2014, cited above). Additionally, *Streptomyces rimosus* DSM40260, a producer of oxytetracycline, was included in the study as a reference strain. Isolates were stored in glycerol at −80° C. in two 96-well plates until further use. To this end, first wells of the 96-well plates were filled with 150 µl lysogeny broth (LB) (10 g/L NaCl, 10 g/L Bacto™ Tryptone, 5 g/L Bacto™ Yeast extract) and inoculated with the strains. Plates were then incubated for two days at 25° C. with gentle agitation, after which 50 µl of 50% (v/v) glycerol was added to achieve a final glycerol concentration of 12.5% (v/v).

TABLE 2

Results of antagonistic activity screening of 130 bacterial isolates[a] against rhizogenic *Agrobacterium* biovar 1 (isolate ST15.13/097)[b]. For more details, the reader is referred to Table 1.

| Phylum/Class | Number of strains tested | Strains with antagonistic activity |
|---|---|---|
| Actinobacteria | | |
| Actinobacteria | 9 | 0 |
| Bacteroidetes | | |
| Flavobacteria | 15 | 0 |
| Sphingobacteria | 1 | 0 |
| Firmicutes | | |
| Bacilli | 7 | 1[c] |

TABLE 2-continued

Results of antagonistic activity screening of 130 bacterial isolates[a] against rhizogenic *Agrobacterium* biovar 1 (isolate ST15.13/097)[b]. For more details, the reader is referred to Table 1.

| Phylum/Class | Number of strains tested | Strains with antagonistic activity |
|---|---|---|
| Proteobacteria | | |
| Alpha-proteobacteria | 12 | 0 |
| Beta-proteobacteria | 61 | 0 |
| Gamma-proteobacteria | 25 | 0 |
| Total | 130 | 1 |

[a]The collection consisted of 130 isolates from soil habitats (de Ridder-Duine et al., 2005, cited above) and has previously been evaluated for antagonistic activity against *Escherichia coli* and *Staphylococcus aureus* (Tyc et al., 2014, cited above).
[b]Antagonistic activity was evaluated using the agar overlay assay (Bosmans et al., 2016b cited above). The strain with antagonistic activity produced a clear zone of inhibition where *Agrobacterium* growth was inhibited.
[c]*Paenibacillus* sp. LMG P-29981.

For evaluating the antagonistic properties of the collection, the 96-well plates were thawed and isolates were spotted using the Genetix QPix 2 colony picking robot (Molecular Devices, UK Limited, Wokingham, United Kingdom) on OmniTray-plates (size 128×86 mm; cap. 90 mL; Greiner bio-one B.V., Alphen a/d Rijn, The Netherlands) with 150 mL solid bacterial growth medium (5 g/L NaCl, 1 g/L KH2PO4; 3 g/L Oxoid Tryptic Soy Broth (TSB); 20 g/L Merck Agar). Next, plates were incubated for 5 days at 20° C. and were used as source plates for spotting test plates containing the same medium mentioned above. Importantly, Merck agar was used in our screening as this agar was shown to support bacterial antagonistic activity against rhizogenic agrobacteria, while several other agars were not (Bosmans et al., 2016b cited above). Spot-inoculated OmniTray plates were then incubated for 1 day at 25° C. Subsequently, 15 mL melted LB agar containing *Agrobacterium* (about 6×10$^5$ cells per mL) was poured over the surface of the plate and incubated again at 25° C. After overnight incubation, the diameter of the inhibition zones was recorded (Bosmans et al., 2016b cited above). Experiments were performed for one rhizogenic *Agrobacterium* biovar 1 strain (ST15.13/097, isolated from tomato; Bosmans, L. et al. (2015) *FEMS Microbiol Ecol* 91 fiv081), and were independently repeated twice.

In a second screening, several isolates from the same genus as the only isolate showing antagonistic activity in the high-throughput screening mentioned above (i.e. *Paenibacillus*) (Table 3) were evaluated for antagonistic activity against *Agrobacterium* biovar 1 strain ST15.13/097 in an agar overlay assay using 9 cm-diameter petri dishes as described by Bosmans et al., (2016b) cited above.

TABLE 3

Antagonistic activity[a] of diverse *Paenibacillus* strains against rhizogenic *Agrobacterium* biovar 1 (isolate ST15.13/097).

| Isolate[b] | *Paenibacillus* | Antagonistic activity |
|---|---|---|
| DSM5050[T] | *Paenibacillus alginolyticus* | − |
| DSM15478 | *Paenibacillus barcinonensis* | + |
| DSM13188[T] | *Paenibacillus borealis* | − |
| DSM17253[T] | *Paenibacillus favisporus* | − |
| DSM22343[T] | *Paenibacillus glacialis* | − |
| LMG12239[T] | *Paenibacillus glucanolyticus* | − |
| DSM17608[T] | *Paenibacillus glycanilyticus* | − |
| DSM15220[T] | *Paenibacillus graminis* | − |
| LMG23886[T] | *Paenibacillus humicus* | − |
| DSM13815[T] | *Paenibacillus jamilae* | − |
| DSM7030 | *Paenibacillus larvae* | − |
| LMG6324[T] | *Paenibacillus macerans* | − |
| LMG6935[T] | *Paenibacillus macquariensis* | − |
| LMG15970 | *Paenibacillus pabuli* | + |
| LMG P-29983 | *Paenibacillus* sp.[c] | + |
| LMG P-29984 | *Paenibacillus* sp.[d] | + |
| LMG P-29982 | *Paenibacillus* sp.[e] | + |
| LMG P-29981 | *Paenibacillus* sp.[f] | + |
| DSM19942 | *Paenibacillus taichungensis* | + |
| DSM7262[T] | *Paenibacillus thiaminolyticus* | − |
| DSM21291 | *Paenibacillus tundrae* | + |
| DSM18927 | *Paenibacillus tylopili* | + |
| LMG9817[T] | *Paenibacillus validus* | − |
| DSM16970[T] | *Paenibacillus xinjiangensis* | − |
| DSM17255 | *Paenibacillus xylanilyticus* | + |

[a]Antagonistic activity was evaluated using the agar overlay assay (Bosmans et al., 2016b cited above). Strains with antagonistic activity produced a clear zone of inhibition where *Agrobacterium* growth was inhibited (+). −, no inhibition zone observed.
[b]AD, NIOO culture collection, Wageningen, The Netherlands; DSM, Deutsche Sammlung von Mikroorganismen und Zellkulturen, Braunschweig, Germany; LMG, Laboratory of Microbiology, Ghent University, Ghent, Belgium; ST, PME&BIM culture collection, Sint-Katelijne Waver, Belgium.
[c]rRNA gene analysis (1390 bp) using EzTaxon revealed highest sequence identity (99.65%) with *Paenibacillus xylanexedens* DSM21292[T] (GenBank Accession No EU558281).
[d]rRNA gene analysis (1390 bp) using EzTaxon revealed highest sequence identity (99.88%) with *Paenibacillus illinoisensis* NBRC15959[T] (GenBank Accession No AB681007).
[e]rRNA gene analysis (1390 bp) using EzTaxon revealed highest sequence identity (99.72%) with *Paenibacillus illinoisensis* NBRC15959[T] (GenBank Accession No AB681007).
[f]rRNA gene analysis (1390 bp) using EzTaxon revealed highest sequence identity (99.85%) with *Paenibacillus xylanexedens* DSM21292[T] (GenBank Accession No EU558281).

Next, for all strains showing antagonistic activity the spectrum of activity was evaluated using 35 rhizogenic *Agrobacterium* biovar 1 strains and 37 other strains from diverse phyla including Actinobacteria, Firmicutes and Proteobacteria, among which several pathogens (Table 4).

TABLE 4

Activity spectrum of selected *Paenibacillus* isolates[a].

| | | | Antagonistic activity | | | | |
|---|---|---|---|---|---|---|---|
| Phylum/Class | Species | Isolate[b] | LMG P-29981 | LMG P-29983 | DSM 17255 | LMG P-29984 | LMG P-29982 |
| Actinobacteria | *Mycobacterium peregrinum* | LMG19256 | − | − | − | − | − |
| Bacteroidetes | | | | | | | |
| Flavobacteria | *Flavobacterium breve* | ST01.08/026 | − | − | − | − | − |
| Firmicutes | | | | | | | |
| Bacilli | *Bacillus amyloliquefaciens* | ST12.14/143 | − | − | − | − | − |
| Bacilli | *Bacillus bataviensis* | EMI_2_2 | − | − | − | − | − |

TABLE 4-continued

Activity spectrum of selected *Paenibacillus* isolates[a].

| Phylum/Class | Species | Isolate[b] | Antagonistic activity | | | | |
| --- | --- | --- | --- | --- | --- | --- | --- |
| | | | LMG P-29981 | LMG P-29983 | DSM 17255 | LMG P-29984 | LMG P-29982 |
| Bacilli | *Bacillus endophyticus* | EMI_1_27 | − | − | − | − | − |
| Bacilli | *Bacillus megaterium* | EMI_2_14 | − | − | − | − | − |
| Bacilli | *Bacillus muralis* | EMI_1_24 | − | − | − | − | − |
| Bacilli | *Bacillus pumilus* | ST12.14/241 | − | − | − | − | − |
| Bacilli | *Bacillus subtilis* | ST01.08/012 | − | − | − | − | − |
| Bacilli | *Bacillus thuringiensis* | ST12.14/323 | − | − | − | − | − |
| Bacilli | *Staphylococcus aureus* | ST01.08/020 | − | − | − | − | − |
| Proteobacteria | | | | | | | |
| Alpha-proteobacteria | *Agrobacterium tumefaciens* | LMG187 | − | − | − | − | − |
| Alpha-proteobacteria | *Rhizobium larrymoorei* | LMG21410 | − | − | − | − | − |
| Alpha-proteobacteria | *Rhizobium meliloti* | LMG4290 | − | − | − | − | − |
| Alpha-proteobacteria | *Rhizobium rubi* | LMG294 | − | − | − | − | − |
| Alpha-proteobacteria | *Rhizobium vitis* | LMG256 | − | + | − | − | − |
| Alpha-proteobacteria | Rhizogenic *Agrobacterium* biovar 1 G[c] | MAFF106580 | + | + | + | − | + |
| Alpha-proteobacteria | Rhizogenic *Agrobacterium* biovar 1 G | MAFF106587 | + | + | + | − | + |
| Alpha-proteobacteria | Rhizogenic *Agrobacterium* biovar 1 G | MAFF301724 | + | + | + | − | + |
| Alpha-proteobacteria | Rhizogenic *Agrobacterium* biovar 1 G | MAFF210265 | + | + | + | − | − |
| Alpha-proteobacteria | Rhizogenic *Agrobacterium* biovar 1 G | MAFF210268 | + | + | + | + | + |
| Alpha-proteobacteria | Rhizogenic *Agrobacterium* biovar 1 G | NCPPB2655 | + | + | + | − | − |
| Alpha-proteobacteria | Rhizogenic *Agrobacterium* biovar 1 G | NCPPB2656 | + | + | + | + | + |
| Alpha-proteobacteria | Rhizogenic *Agrobacterium* biovar 1 G | NCPPB2659 | + | + | + | + | + |
| Alpha-proteobacteria | Rhizogenic *Agrobacterium* biovar 1 G | NCPPB2660 | + | + | + | − | − |
| Alpha-proteobacteria | Rhizogenic *Agrobacterium* biovar 1 G | NCPPB4043 | + | + | + | − | − |
| Alpha-proteobacteria | Rhizogenic *Agrobacterium* biovar 1 G | NCPPB4042 | + | + | + | − | − |
| Alpha-proteobacteria | Rhizogenic *Agrobacterium* biovar 1 R | ST15.13/001 | + | + | + | + | + |
| Alpha-proteobacteria | Rhizogenic *Agrobacterium* biovar 1 R | ST15.13/006 | + | + | + | − | − |
| Alpha-proteobacteria | Rhizogenic *Agrobacterium* biovar 1 R | ST15.13/007 | + | + | + | − | − |
| Alpha-proteobacteria | Rhizogenic *Agrobacterium* biovar 1 R | ST15.13/012 | + | + | + | + | + |
| Alpha-proteobacteria | Rhizogenic *Agrobacterium* biovar 1 R | ST15.13/013 | + | + | + | + | − |
| Alpha-proteobacteria | Rhizogenic *Agrobacterium* biovar 1 R | ST15.13/039 | + | + | + | + | + |
| Alpha-proteobacteria | Rhizogenic *Agrobacterium* biovar 1 R | ST15.13/040 | + | + | + | + | − |
| Alpha-proteobacteria | Rhizogenic *Agrobacterium* biovar 1 R | ST15.13/042 | + | + | + | + | − |
| Alpha-proteobacteria | Rhizogenic *Agrobacterium* biovar 1 R | ST15.13/046 | + | + | + | + | + |
| Alpha-proteobacteria | Rhizogenic *Agrobacterium* biovar 1 R | ST15.13/048 | + | + | + | + | + |
| Alpha-proteobacteria | Rhizogenic *Agrobacterium* biovar 1 R | ST15.13/054 | + | + | + | + | + |
| Alpha-proteobacteria | Rhizogenic *Agrobacterium* biovar 1 R | ST15.13/056 | + | + | + | + | + |
| Alpha-proteobacteria | Rhizogenic *Agrobacterium* biovar 1 R | ST15.13/057 | + | + | + | + | − |
| Alpha-proteobacteria | Rhizogenic *Agrobacterium* biovar 1 R | ST15.13/059 | + | + | + | − | − |
| Alpha-proteobacteria | Rhizogenic *Agrobacterium* biovar 1 R | ST15.13/060 | + | + | + | + | + |
| Alpha-proteobacteria | Rhizogenic *Agrobacterium* biovar 1 R | ST15.13/064 | + | + | + | + | + |
| Alpha-proteobacteria | Rhizogenic *Agrobacterium* biovar 1 R | ST15.13/077 | + | + | + | + | + |
| Alpha-proteobacteria | Rhizogenic *Agrobacterium* biovar 1 R | ST15.13/090 | + | + | + | − | − |
| Alpha-proteobacteria | Rhizogenic *Agrobacterium* biovar 1 R | ST15.13/091 | + | + | + | − | − |
| Alpha-proteobacteria | Rhizogenic *Agrobacterium* biovar 1 R | ST15.13/095 | + | + | + | − | + |
| Alpha-proteobacteria | Rhizogenic *Agrobacterium* biovar 1 R | ST15.13/097 | + | + | + | − | − |
| Alpha-proteobacteria | Rhizogenic *Agrobacterium* biovar 1 R | ST15.13/098 | + | + | + | − | − |
| Alpha-proteobacteria | Rhizogenic *Agrobacterium* biovar 1 R | NCPPB4062 | + | + | + | + | − |
| Alpha-proteobacteria | Rhizogenic *Agrobacterium* biovar 1 R | ST15.13/045 | + | + | + | + | − |
| Alpha-proteobacteria | Rhizogenic *Agrobacterium* biovar 2 | NCPPB2991 | + | + | + | − | − |
| Alpha-proteobacteria | Rhizogenic *Agrobacterium* biovar 2 | LMG150 | − | − | − | − | − |
| Alpha-proteobacteria | Rhizogenic *Agrobacterium* biovar 2 | NCPPB2303 | − | − | − | − | − |
| Alpha-proteobacteria | Rhizogenic *Agrobacterium* biovar 2 | LMG149 | − | − | − | − | − |
| Alpha-proteobacteria | Rhizogenic *Agrobacterium* biovar 2 | LMG138 | + | + | − | − | − |
| Alpha-proteobacteria | Rhizogenic *Agrobacterium* biovar 2 | ST15.13/027 | − | − | − | − | − |
| beta-proteobacteria | *Burkholderia bryophila* | ST15.15/021 | − | − | − | − | − |
| beta-proteobacteria | *Burkholderia insulsa* | ST15.15/014 | − | − | − | − | − |
| beta-proteobacteria | *Collimonas arenae* | ST15.15/017 | − | − | − | − | − |
| beta-proteobacteria | *Collimonas fungivorans* | ST15.15/016 | − | − | − | − | − |
| beta-proteobacteria | *Collimonas pratensis* | ST15.15/019 | − | − | − | − | − |
| beta-proteobacteria | *Janthinobacterium lividum* | ST15.15/039 | − | − | − | − | − |
| Gamma-proteobacteria | *Escherichia coli* | ST08.12/001 | − | − | − | − | − |
| Gamma-proteobacteria | *Pseudomonas aeruginosa* | ST01.08/008 | − | − | − | − | − |
| Gamma-proteobacteria | *Pseudomonas fluorescens* | ST12.14/123 | − | − | − | − | − |
| Gamma-proteobacteria | *Pseudomonas lurida* | EPU_2_30 | − | − | − | − | − |
| Gamma-proteobacteria | *Pseudomonas orientalis* | ST12.14/122 | − | − | − | − | − |
| Gamma-proteobacteria | *Pseudomonas plecoglossicida* | ST12.14/336 | − | − | − | − | − |

TABLE 4-continued

Activity spectrum of selected *Paenibacillus* isolates[a].

| | | | Antagonistic activity | | | | |
|---|---|---|---|---|---|---|---|
| Phylum/Class | Species | Isolate[b] | LMG P-29981 | LMG P-29983 | DSM 17255 | LMG P-29984 | LMG P-29982 |
| Gamma-proteobacteria | *Pseudomonas poae* | 9.1.2-B1 | − | − | − | − | − |
| Gamma-proteobacteria | *Pseudomonas putida* | ST12.14/260 | − | − | − | − | − |
| Gamma-proteobacteria | *Pseudomonas veronii* | EHE_1_3 | − | − | − | − | − |

[a]Antagonistic activity was evaluated using the agar overlay assay (Bosmans et al., 2016b, cited above). Antagonistic effects were observed as a clear zone of inhibition where growth of the tested bacterium was inhibited (+). −, no inhibition zone observed
[b]AD, NIOO culture collection, Wageningen, The Netherlands; LMG, Laboratory of Microbiology, Ghent University, Ghent, Belgium; MAFF, NIAS Genebank (National Institute of Agrobiological Sciences), Ibaraki, Japan; NCPPB, National Collection of Plant Pathogenic Bacteria, York, UK; EMI, EPU, EHE and ST, PME&BIM culture collection, Sint-Katelijne Waver, Belgium.
[c]*Agrobacterium* biovar 1 strains isolated from Cucurbitaceae (melon, cucumber) and Solanaceae (tomato crops) (for more information, see Bosmans et al., 2015 cited above) are indicated by G and R, respectively.

Characterization of Antagonistic Isolates

For all isolates with antagonistic activity the 16S ribosomal RNA (rRNA) genes were partially amplified and sequenced as described by Bosmans et al., (2015) cited above. Obtained sequences were individually trimmed for quality, using a minimum Phred score of 20, and, in cases of ambiguous base calls, manually edited based on the obtained electropherograms. Next, a maximum likelihood tree was constructed using MEGA v5.2 (Tamura K. et al. (2011) Molecular Biology and Evolution 28: 2731-2739) to assess the phylogenetic relatedness between the antagonistic isolates as well as their phylogenetic relationships with previously characterized reference (type) strains for which the sequences were retrieved from Eztaxon.

Further, antagonistic isolates were subjected to a Bioscreen C analysis (Oy Growth Curves Ab Ltd, Finland) to assess growth characteristics in different media. The working volume in the wells of the Bioscreen plate was 200 µL, comprised of 5 µL bacterial suspension (about $10^5$ cells per mL LB medium) and 195 µL of one of the following three media: TSB (Oxoid, Basingstoke, UK), LB and a minimal broth medium (M70) containing 2 g/L Bacto™ Yeast extract and 10 g/L Mannitol (Sigma, Mo., VS). The temperature was controlled at 25° C., and the optical density of the cell suspensions was measured automatically at 600 nm in regular intervals of 15 min, for three days. Before each measurement, the Bioscreen plate was automatically shaken for 60 seconds. The experiments were performed two times independently, each with three replicates. Tested culture medium without inoculum was used as a reference. Growth curves were generated by monitoring the averaged optical density (OD600) as a function of incubation time.

Preliminary Characterization of the Antagonistic Compound(s)

The two best performing strains (based on the size of the zone of inhibition, specificity and growth in the previous assays), LMG P-29981 and LMG P-29983, were selected for preliminary characterization of the antagonistic compounds. First, isolates were investigated for production of volatile organic compounds (VOCs) having antagonistic activity against *Agrobacterium*. To this end, two bottoms of a 9 cm-diameter petri dish containing a freshly spot-inoculated (15 µL per spot; about $10^5$ cells per mL in TSB) antagonistic bacterium (on the medium described above) or a rhizogenic *Agrobacterium* biovar 1 isolate (ST15.13/097) (on TSA, Oxoid, Basingstoke, UK) were sealed facing each other and incubated at 25° C. with the petri dish containing the antagonistic bacterium at the bottom. The experiments were carried out using two independent repeats, each with three replicates. Growth inhibition was calculated by measuring the zone of inhibition after 1, 2 and 3 days of incubation.

Secondly, to test secretion of antagonistic compounds into the medium, cell-free culture filtrates were prepared and tested for antibacterial activity in a microtitre plate (Thermo Scientific™ Nunc™ MicroWell™ 96-Well Microplates). To this end, antagonistic bacteria were cultured in liquid medium (100 mL) consisting of 3 g/L tryptic soy broth (TSB; Oxoid, Basingstoke, UK), 5 g/L NaCl, and 1 g/L KH2PO4, and incubated at 25° C. for 2 days. Cultures of about $10^4$ cells per mL were then filter-sterilized (0.2-µm filter, sterile mixed cellulose ester membrane, Whatman, GE Healthcare Life Sciences, UK), and a portion of the filtrate was added to the wells of the microtiter plate. More specifically, 100, 150 and 190 µL of the cell-free filtrates were added to 100, 50 and 10 µL LB containing *Agrobacterium* biovar 1 isolate ST15.13/097 (final concentration of $5 \times 10^2$ cells per mL for each condition), respectively. In the control wells, the culture filtrate was replaced by LB. For all treatments, plates were incubated with gentle agitation and growth was photospectrometrically (OD600) monitored after 24 h of incubation at 25° C. Experiments were independently repeated twice.

Extraction and Purification of the Antagonistic Compound(s)

For the extraction and identification of the compounds responsible for the antagonistic activity, the two best performing strains, LMG P-29981 and LMG P-29983 were selected and spot-inoculated (15 µL per spot) on the agar medium mentioned above in 9 cm-diameter petri dishes (60 plates per strain). Following inoculation with *Agrobacterium* (isolate ST15.13/097) (see above) and subsequent incubation for 1 day at 25° C., 60 agar pieces of approximately 1 cm2 were excised from the zone of inhibition, suspended in 65% methanol (65% methanol, 34.9% milliQ water and 0.1% formic acid) and then shaken for 3 h at room temperature. After centrifugation at 4800 rpm for 15 min, the liquid phase was transferred and the methanol was evaporated. Subsequently, the aqueous phase was frozen and freeze-dried, and the dried extract was dissolved again in 65% methanol prior to further analysis. Obtained extracts were analysed by reversed-phase high-performance liquid chromatography (RP-HPLC) (Waters Chromatography B.V., Etten-Leur, the Netherlands) equipped with a Waters 996 photodiode array detector. The separations were performed on a Waters Symmetry C18RP column (5 µm, 3.9×150 mm)

with a mobile phase of 70% methanol and 0.1% formic acid and a flow of 0.2 mL/min for 10 min (or 60 min for improved resolution of peaks) was applied over. UV detection took place at 240 nm. For each collected fraction, methanol was evaporated and the remaining (aqueous) phase was freeze-dried, dissolved again in 65% methanol, and used in the agar overlay assay as described above, with that difference that the collected phases were spotted (20 µL on a filter paper) instead of the bacterial inoculum.

For the positive fraction of the HPLC-analysis, mass spectra were acquired in positive ionization mode on a quadrupole orthogonal acceleration time-of-flight mass spectrometer (Syntapt G2, Waters, Milford, Mass.) equipped with a standard electrospray probe and controlled by the MassLynx 4.1 software. Resolution of the instrument was set to 15000 (resolution mode). The capillary voltage and cone voltage were set to 3 kV and 35 V, respectively. Accurate masses were obtained using the LockSpray source and leucine enkephalin (2 ng/µL in acetonitrile:water 1:1) as reference compound infused at 3 µL/min. The chromatographic system consisted of an ultra-performance liquid chromatography (UPLC) system (Acquity H-class, Waters, Milford, Mass.). Separations were performed on a reversed phase C18 column (Acquity HSS T3 1.8 µm 1×50 mm) at a flow rate of 150 µL/min. The injection volume was 5 µL. A linear gradient of acetonitrile in water (2 to 22% in 10 min) was applied. Mass spectra in the mass range m/z 100 to 700 were acquired at a rate of one spectrum per second.

Evaluation of the Antagonistic Activity in Greenhouse Conditions

A greenhouse experiment was performed to assess the biocontrol activity of a mixture of the two selected bacteria (LMG P-29981 and LMG P-29983) against *Agrobacterium* biovar 1 in a commercial hydroponic tomato production system in Belgium. Experiments were performed using the tomato cultivar 'Rebelski' (De Ruiter), rootstock Maxifort (De Ruiter). There are four plants in one rockwool mat with a plant density of 2.5 plants/m². From the start of the experiment, i.e. from the moment of planting of ca 60-day-old tomato seedlings (January 2016), a set of 20 plants were treated daily for 10 days with a mixture of 50 mL of the candidate BCO's ($10^8$ cells/mL each), while another set of 20 plants remained untreated. From day ten of the experiment, all 40 plants were artificially infected by applying a rhizogenic *Agrobacterium* biovar 1 strain (isolate ST15.13/097) (50 mL of a suspension of $10^8$ cells/mL) once a week for a total of six weeks. Plants were visually evaluated every two weeks for a total period of 8 weeks after artificial infection with rhizogenic *Agrobacterium* for development of extreme root formation, and plants were considered infected when visual HRD symptoms were confirmed by a positive qPCR analysis of the pathogen from investigated root material (Bosmans, L. et al (2016a) *Eur J Plant Pathol* 145, 719-730). Considering that eggplant is generally cultivated on a tomato rootstock, the root system in the commercial hydroponics production of eggplant is equally protected against HRD by the *Paenibacillus* strains described here. In a similar way as described above, *Paenibacillus* biocontrol isolates described in this patent are able to control hairy root disease in commercial hydroponics cucumber cultivation. This is done by treating the plants daily for 10 days with a mixture of 50 mL of the candidate BCO ($10^8$ cells/mL each), and subsequently artificially infected by applying a rhizogenic *Agrobacterium* biovar 1 strain (50 mL of a suspension of $10^8$ cells/mL) once a week for a total of six weeks. After visual inspection of the plants for extreme root formation and subsequent confirmation with qPCR, a significant reduction in incidence of HRD can be observed between the untreated plants and plants treated with BCO's.

Example 2. Antagonistic Activity Against Rhizogenic Agrobacteria

Figure 3:
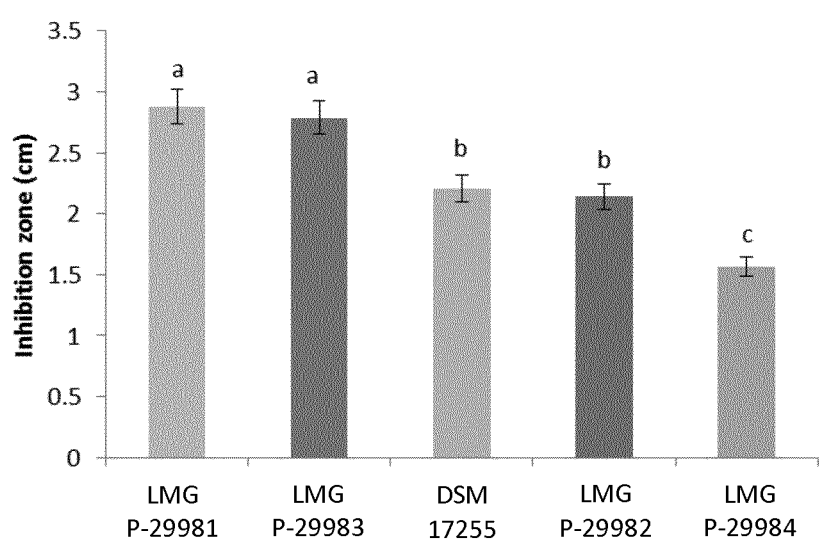
FIG. 3. Antagonistic activity of five selected *Paenibacillus* isolates against rhizogenic *Agrobacterium* biovar 1 (strain ST15.13/097) using the overlay assay described by Bosmans L. et al (2016b) *J Microbiol Meth* 127, 7-9. Presented data are means of the observed inhibition zones (n=2). Error bars represent standard errors of the mean. Different letters indicate significant differences (Student t-test) among strains (P<0.05).
Figure 4:
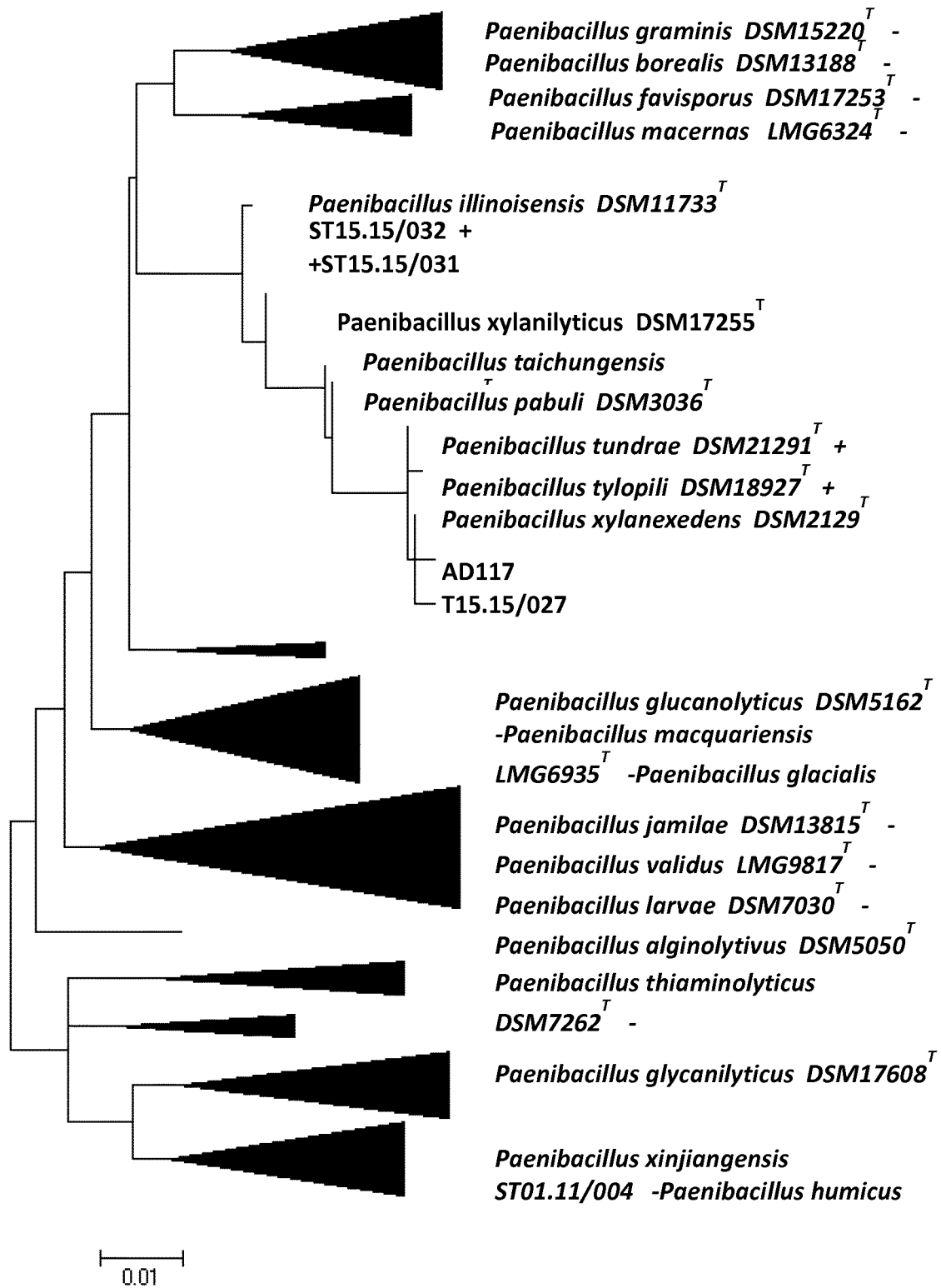
FIG. 4. Phylogenetic positioning of *Paenibacillus* isolates showing antagonistic activity against rhizogenic *Agrobacterium* biovar 1 strains. A maximum likelihood (ML) tree was constructed based on 16S rRNA gene sequences (1390 bp) for all reference (type) strains of all *Paenibacillus* species currently described (160 species) and all other *Paenibacillus* strains included in this study (Table 3). Due to the extent of the tree, several clades were collapsed. A tight cluster of *Paenibacillus* strains was found to have antagonistic activity against rhizogenic agrobacteria (+), while strains that were less related to this cluster did not (−). Particular *Paenibacillus* strains representative for the different phylogenetic groups that were tested for antagonistic activity against *Agrobacterium* biovar 1 (isolate ST15.13/097) are indicated on the tree.

Out of 130 bacterial strains tested belonging to different phyla and different classes, isolate LMG P-29981 belonging to the genus *Paenibacillus*, showed antibacterial activity against the tested rhizogenic *Agrobacterium* isolate (ST15.13/097) (Table 1 and 2). Additional screening of several *Paenibacillus* strains resulted in four additional antagonistic strains, including *P. xylanilyticus* DSM17255T and the *Paenibacillus* isolates LMG P-29983, LMG P-29984 and LMG P-29982 (Table 3). Overall, for these strains the average diameter of the inhibition zones varied between 1.57 cm and 2.88 cm, with the largest zones of inhibition for isolates LMG P-29981 (2.88 cm) and LMG P-29983 (2.79 cm) (FIG. 3). 16S rRNA gene sequence analysis using the EZTaxon database showed that these strains that were not yet assigned to the species level had highest sequence homology with *Paenibacillus illinoisensis* (LMG P-29984 and LMG P-29982) and *P. xylanexedens* (LMG P-29981 and LMG P-29983) (Table 3). Phylogenetic positioning of the strains in a phylogenetic tree containing 16S rRNA gene sequences of the reference (type) strains of all validly named *Paenibacillus* species (160 species) revealed that these five strains clustered tightly with *P. illinoisensis, P. xylanilyticus, P. taichungensis, P. pabuli, P. tundra, P. tylopili* and *P. xylanexedens* (FIG. 4). When also the type strains of these species were subjected to the agar overlay assay, all strains demonstrated antagonistic activity, while strains that were less related to this cluster did not (Table 3).

Assessment of the spectrum of antagonistic activity of isolates LMG P-29981, DSM15255T, LMG P-29983, LMG P-29984 and LMG P-29982 revealed that three isolates (LMG P-29981, DSM17255T and LMG P-29983) showed antagonistic activity against all rhizogenic *Agrobacterium* biovar 1 isolates tested (Table 4). In contrast, the two isolates corresponding to *P. illinoisensis*, LMG P-29984 and LMG P-29982, showed a different activity spectrum and were only able to inhibit the growth of 19 and 17 *Agrobacterium* biovar 1 isolates, respectively (Table 4). Furthermore, isolates LMG P-29981, DSM17255T and LMG P-29983 were able to suppress the growth of one or more rhizogenic *Agrobacterium* biovar 2 strains causing HRD on Rosaceae. Additionally, strain LMG P-29983 showed antagonistic activity against *Rhizobium vitis*, a plant pathogen causing crown gall of grapevine (Table 4). Examination of the growth characteristics of the five selected strains revealed that highest growth rates were observed for LMG P-29981, DSM17255T and LMG P-29983, irrespective of the growth medium used (data not shown).

Example 3. Preliminary Characterization of the Antagonistic Compound(S)

Based on the results described above (size of the zone of inhibition, spectrum of activity and general growth characteristics), both isolate LMG P-29981 and LMG P-29983 were selected for further experiments to better understand the antagonistic effects observed. First, isolates were evaluated for production of volatile organic compounds (VOCs) having antagonistic activity against rhizogenic agrobacteria, but no antagonistic VOCs could be detected. In contrast, when the cell-free culture filtrates were tested, a dose-dependent response of *Agrobacterium* was observed (FIG. 1), suggesting that the selected bacteria secrete water-soluble antibacterial compounds. When an extract was made from agar obtained from the inhibition zones in the agar overlay assay, several fractions could be obtained, which were all tested again in an agar overlay assay against rhizogenic *Agrobacterium* biovar 1 isolate ST15.13/097. One fraction was found to show antagonistic activity. Mass spectrometry analysis of this HPLC fraction showed the presence of four specific peaks having a mass number of m/z=463.2030, 477.1830, 504.2669 and 578.2324.

Example 4. Greenhouse Experiments

Figure 2:
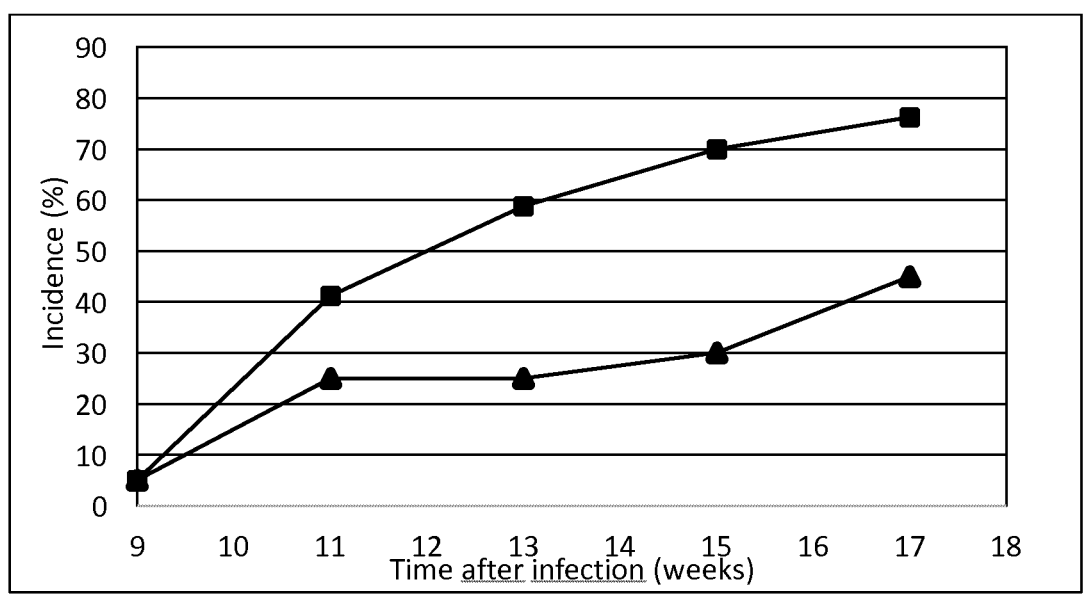
FIG. 2. Assessment of the antagonistic activity of a mixture of *Paenibacillus* isolates (LMG P-29981 and LMG P-29983) against rhizogenic agrobacteria (isolate ST15.13/097) in greenhouse conditions. Incidence of HRD (calculated as the ratio of infected plants) is plotted in function of time (weeks after initial infection): □, control plants (n=20); ▲, plants treated with the BCO mixture (n=20). Since day 10 of the experiment, all plants were weekly infected with *Agrobacterium* (isolate ST15.13/097) for 6 weeks in total. Plants were visually evaluated every two weeks for development of extreme root formation. Observation of symptoms was confirmed by a positive qPCR analysis targeting *Agrobacterium* biovar 1 DNA.

A mixture of LMG P-29981 and LMG P-29983 was evaluated for its biocontrol potential of rhizogenic agrobacteria in greenhouse conditions. To this end, two sets of 20 plants were scored weekly for development of extreme root formation. Nine weeks after the artificial infection of the experiment, the first symptoms of HRD were observed. 17 weeks after artificial infection with *Agrobacterium* about 75% of all control plants artificially infected with *Agrobacterium* showed HRD. When plants were treated with a mixture of LMG P-29981 and LMG P-29983 incidence of HRD dropped to 45% (FIG. 2), suggesting high biocontrol potential of the used inoculum. Observation of HRD symptoms was always confirmed by a positive qPCR analysis targeting *Agrobacterium* biovar 1 DNA.

Example 5. Definition of *Paenibacillus* Spp. With Antagonistic Activity Against *Agrobacterium* Biovar 1

To the best of our knowledge, our study is the first in which a correlation was found between a distinct phylogenetic clade and antagonistic activity against a particular bacterial pathogen. The *Paenibacillus* strains with antagonistic activity against *Agrobacterium* biovar 1 can be identified based on a particular sequence within the 16S rRNA gene (position 134-172). All strains having a sequence identity of 93% or more to the consensus signature in the 16S rRNA gene (5'-TTGGGACAACTACCG-GAAACGGTAGCTAATACCGAATA-3' (SEQ No 1.) are strains with antagonistic activity against *Agrobacterium* bio3var 1. Even more in particular, all strains have a sequence identity of 100% to the consensus signature in the 16S rRNA gene (SEQ ID NO: 1). Most related strain without activity: 4 different bases of this 38 (89.5%) (Table 5).

Example 6. Modes of Application

We have shown that pouring of a *Paenibacillus* BCO suspension directly onto the substrate on which tomato seedlings are grown is an effective procedure to protect tomato plants against HRD. However, the BCO's can also be added to the irrigation water in the desired concentration to disperse the BCO's through the irrigation system and the hydroponics substrate. This allows for automated and continuous dosing, which may result in an even higher effectiveness of the BCO. Alternatively, the *Paenibacillus* BCO can be applied to the hydroponics substrate before planting the tomato seedlings. During the production system of the hydroponics substrate, the BCO's can be mixed with perlite, cocos, rockwool, which is used to produce the hydroponics substrate. Finally, the BCO can be used to coat tomato seed, thereby protecting the young seedlings to HRD.

TABLE 5

Partial 16S rRNA gene sequences of Paenibacillus strains. The partial 16S rRNA gene sequences with at least 93% sequence identity to the sequence of SEQ ID NO: 1 are indicated in the square. Said Paenibacillus strains show a 100% sequence identity with the sequence of SEQ ID NO: 1.

| Paenibacillus strain | SEQ ID NO | Partial 16S rRNA gene sequence |
|---|---|---|
| P. taicchungensis_EU179327 [*] | 2 | CACGTAGGCAACCTGCCTCAAGCTGGGACAACAACTGGGACAACTGGGGAAACGGTAGCTAATACCGAATAGTTGTTTTCTTCCTGAAGAGAACTGGA |
| P. illinoiseensis_D85397 | 3 | CACGTAGGCAACCTGCCTGCCCTCAAGCTTGGGACAACAACTAGTTAATACCGAATACTTGCTTCCTTCCTGCCTGAAGGAAGCTGGA |
| P. xylanilyticus_AY427832 | 4 | CACGTAGGCAACCTGCCTGCCCTCAAGCTTGGGACAACAACTAGCTAATACCGAATACTTGCTTCTTTCGCCTGAAGGAAGCTGGA |
| P. xylanexedens_CLG_48537 | 5 | CACGTAGGCAACCTGCCTGCCCTCAAGTTTGGGACAACAACTAGCTAATACCGAATAATTGTTTTTCTTCGCCTGAAGGAACTGGA |
| P. pabuli_BCNM100057 | 6 | CACGTAGGCAACCTGCCTGCCCTCAAGTTTGGGACAACAACTAGCTAATACCGAATAGTTGTTTTCTTCGCCTGAAGAGAACTGGA |
| P. tylopili_EF206295 | 7 | CACGTAGGCAACCTGCCTGCCCTCAAGTTTGGGACAACAACTAGCTAATACCGAATAGTTGTTTTTCTTCCTGAAGAGAACTGGG |
| P. tundrae_EU558284 | 8 | CACGTAGGCAACCTGCCTGCCCTCAAGTTTGGGACAACAACTAGCTAATACCGAATACTTGTTTCTTCTTGTTTTCTTCCTGAAGAGAACTGGA |
| P. jamilae_AJ271157 | 9 | CACGTAGGCAACCTGCCCTCAAGTTTGGGACAACAACTAGCTAATACCGAATAGTTGTTTCTTCTTCTTCCTGAAGAGAACTGGA |
| P. glucanolyticus_AB073189 | 10 | CACGTAGGCAACCTGCCCACCAAGACAGGGACTGGGATAACTAGCTAATACCGAATAACATCCCTTTTCCTGCATGGAGAAGGAGGA |
| P. borealis_CP009285 | 11 | CACGTAGGCAACCTGCCTGCCTCAAGACTGGGACTGGGATAACTAGCTAATACCGAATAATTTATTACATAGCATTATGTATAATGA |
| P. graminis_CP009287 | 12 | CACGTAGGCAACCTACCCCTCTAGACTGTAAGAACTGGGATAACTAGCTAATACCGAATAATTCTTTCTCCTGAAGAGAGAATGA |
| P. macq._defensor_AB360546 | 13 | CACGTAGGCAACCTGCCTGCCCGGTAAGACCGGGATAACTAGCTAATACCGAATAAATTCCCTGACCCCCCCCTGGGCTAGGATGA |
| P. glacialis_EU815300 | 14 | CACGTAGGTAACCTGCCTGCTGTAAGACTGGGATAACTAGCTAATACCGAATAAATTGTTTCTTCCATGAAGAAGACACTGA |
| P. macerans_AB073196 | 15 | CACGTAGGCAACCTACCCGCCTAAGACCGGGATAACTAGCTAATACCGAATAATCAAGTCTTCCCATGGAGCTTGGGA |
| P. favisporus_AY208751 | 16 | CACGTAGGCAACCTGCCTGCCTGCAAGAACCCACGGAGTGAGCTAATACCGAATATCCATTTCCTCCTGAGGGATGATGA |
| P. thiaminolyticus_AB073197 | 17 | TACGTAGGTAACCTGCCCTTAAGACTGGGACTGGGATAACTCACGGAATGCTAATACCGAATAGTCGATTTCCTCGCATGAGGAATCGGGA |
| P. humicus_AM411528 | 18 | CACGTAGGCAACCTGCCTGCCTGCAAGAACCTCCGGATAACTTGGGATAACAATCGGAATAACTGCTAATACCGAATATGCGGATCTCCTCCCCTGAGGGATCGGGA |
| P. xinjiangensis_AY839868 | 19 | CACGTGGGTAACCTGCCCCCATAAGACTGGGCATAACTGGGACAATGCTAATACCGGATACGCAATTTGGTCCATGGCCGARTTGGGA |
| P. glycanilyticus_AB042938 | 20 | CACGTAGGTAACCTGCCCCATAAGACTGGGACTGGGATAACAATTCGGAATCGAATGCTAATACCGGATACCGGCGAATCGTCGCCATGATCGAATCGGGA |
| P. larvae_CP019687 | 21 | CACGTAGGCAACCTGCCTGCCTCAAGACTGTGTAAGAACCTGTGCGAAAACTTGCGAAAACAATTCGAATAACTGCTAATACCGGATAACCTGGGTTTCTTCGCATGAAGAAGTCATGA |
| P. alginolyticus_D78465 | 22 | CACGTAGGT?A?CTGCCTATAAGATGCGGATAATATCCGAAATATCCGAAATCGAAACCGGATAAATTGGTTT?CTGCCATGAGAGAACTATGA |
| P. vaidus_AB073203 | 23 | ACGTAGGCAACCTGCCTGTAAGATCGGGATAACTACCGGAAACGATAAGACCGGATAAGACCGGATAAGACCGGAAAACTGGTAGATCTGGTTTCCCGCATGGGAATCATGAA |

TABLE 5-continued

Partial 16S rRNA gene sequences of Paenibacillus strains. The partial 16S rRNA gene sequences with at least 93% sequence identity to the sequence of SEQ ID NO: 1 are indicated in the square. Said Paenibacillus strains show a 100% sequence identity with the sequence of SEQ ID NO: 1.

| Applicant's or agent's file reference LRD-036 | International application No. PCT/EP2017/084394 |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 5, line 11-16.

B. IDENTIFICATION OF DEPOSIT — Further deposits are identified on an additional sheet [X]

Name of depositary institution
BCCM Belgian Coordinated Collections of Microorganisms (BCCM)

Address of depositary institution (including postal code and country)
Laboratorium voor Microbiologie - Bacteriënverzameling (LMG)
Universiteit Gent
K.L. Ledeganckstraat 35
9000 Gent
Belgium

| Date of deposit 14/12/2016 | Accession Number LMG P-29981 |
|---|---|

C. ADDITIONAL INDICATIONS (leave blank if not applicable)  This information is continued on an additional sheet [ ]

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
[X] This sheet was received with the international application For International Bureau use only
[ ] This sheet was received by the International Bureau on:

Authorized officer
Kuiper-Cristina, Nathalie

Authorized officer

Form PCT/RO/134 (July1998; reprint Jan SUBSTITUTE SHEET (RULE 26)

| Applicant's or agent's file reference LRD-036 | International application No. PCT/EP2017/084394 |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 5, line 11-16.

B. IDENTIFICATION OF DEPOSIT — Further deposits are identified on an additional sheet ☒

Name of depositary institution
BCCM Belgian Coordinated Collections of Microorganisms (BCCM)

Address of depositary institution (including postal code and country)
Laboratorium voor Microbiologie - Bacteriënverzameling (LMG)
Universiteit Gent
K.L. Ledeganckstraat 35
9000 Gent
Belgium

| Date of deposit 14/12/2016 | Accession Number LMG P-29982 |
|---|---|

C. ADDITIONAL INDICATIONS (leave blank if not applicable)    This information is continued on an additional sheet ☐

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only
☒ This sheet was received with the international application Authorized officer
Kuiper-Cristina, Nathalie For International Bureau use only
☐ This sheet was received by the International Bureau on:

Authorized officer

SUBSTITUTE SHEET (RULE 26)

| Applicant's or agent's file reference LRD-036 | International application No. PCT/EP2017/084394 |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 5, line 11-16.

B. IDENTIFICATION OF DEPOSIT     Further deposits are identified on an additional sheet [X]

Name of depositary institution
BCCM Belgian Coordinated Collections of Microorganisms (BCCM)

Address of depositary institution (including postal code and country)
Laboratorium voor Microbiologie - Bacteriënverzameling (LMG)
Universiteit Gent
K.L. Ledeganckstraat 35
9000 Gent
Belgium

| Date of deposit | Accession Number |
|---|---|
| 14/12/2016 | LMG P-29983 |

C. ADDITIONAL INDICATIONS (leave blank if not applicable)    This information is continued on an additional sheet [ ]

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
[X] This sheet was received with the international application Authorized officer
Kuiper-Cristina, Nathalie For International Bureau use only
[ ] This sheet was received by the International Bureau on:

Authorized officer

| Applicant's or agent's file reference LRD-036 | International application No. PCT/EP2017/084394 |
|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page 5 , line 11-16 .

B. IDENTIFICATION OF DEPOSIT     Further deposits are identified on an additional sheet ☒

Name of depositary institution
BCCM Belgian Coordinated Collections of Microorganisms (BCCM)

Address of depositary institution *(including postal code and country)*
Laboratorium voor Microbiologie - Bacterienverzameling (LMG)
Universiteit Gent
K.L. Ledeganckstraat 35
9000 Gent
Belgium

| Date of deposit 14/12/2016 | Accession Number LMG P-29984 |
|---|---|

C. ADDITIONAL INDICATIONS *(leave blank if not applicable)*     This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

---

For receiving Office use only
☒ This sheet was received with the international application Authorized officer
    Kuiper-Cristina, Nathalie For International Bureau use only
☐ This sheet was received by the International Bureau on:

Authorized officer

Form PCT/RO/134 (July 1998; reprint January SUBSTITUTE SHEET (RULE 26)

The invention claimed is:

1. A method of treating hairy root disease (HRD) or reducing the incidence of rhizogenic *Agrobacterium* infection in a plant, comprising administering to the plant an effective amount of at least one isolated *Paenibacillus* strain or of an extract thereof having antagonistic activity against *Agrobacterium* infection of at least one isolated *Paenibacillus* strain, wherein said at least one *Paenibacillus* strain comprises a 16S rRNA sequence with at least 95% sequence identity to the sequence of SEQ ID NO: 1.

2. The method according to claim 1 wherein the at least one *Paenibacillus* strain comprises a 16S rRNA sequence with 100% sequence identity to the sequence of SEQ ID NO: 1.

3. The method according to claim 1, wherein the at least one *Paenibacillus* strain is selected from the group consisting of *Paenibacillus illinoisensis* having collection number DSM11733, *Paenibacillus pabuli* having collection number LMG15970, *Paenibacillus xylanexedens* having collection number LMG P-29983, *Paenibacillus illinoisensis* having collection number LMG P-29984, *Paenibacillus illinoisensis* having collection number LMG P-29982, *Paenibacillus xylanexedens* having collection number LMG P-29981, *Paenibacillus taichungensis* having collection number DSM19942, *Paenibacillus tundrae* having collection number DSM21291, *Paenibacillus tylopili* having collection number DSM18927 and *Paenibacillus xylanilyticus* having collection number DSM17255 or a derivative, variant or mutant of any thereof.

4. The method according to claim 1, wherein the administering to the plant is by a method selected from the group consisting of: applying directly onto a substrate on which seedlings are grown, adding to the irrigation water, applying to the hydroponics substrate, application to seed, and foliar spraying.

* * * * *

UNITED STATES PATENT AND TRADEMARK OFFICE
CERTIFICATE OF CORRECTION

PATENT NO. : 11,530,383 B2
APPLICATION NO. : 16/472630
DATED : December 20, 2022
INVENTOR(S) : Lien Bosmans et al.

Page 1 of 1

It is certified that error appears in the above-identified patent and that said Letters Patent is hereby corrected as shown below:

On the Title Page

Item (71), applicant, name, delete "Proefstation Hoogstraten", and insert --Proefcentrum Hoogstraten--, therefor.

Item (73), assignee 2, name, delete "NEDERLANDS INSTITUTE OF ECOLOGY (NIOO-KNAW)", and insert --NEDERLANDS INSTITUUT VOOR ECOLOGIE (NIOOKNAW)--, therefor.

Item (73), assignee 3, city, delete "Sint Katelijne", and insert --Sint-Katelijne-Waver--, therefor.

Item (73), assignee 4, city, delete "Sint Katelijne", and insert --Sint-Katelijne-Waver--, therefor.

Item (74), attorney, agent, or firm, delete "DINSMORE & SHOHL, LLP", and insert --DINSMORE & SHOHL LLP--, therefor.

In the Specification

In Column 12, Line(s) 45, before "different", delete "an", insert --a--, therefor.

In Column 12, Line(s) 55, before "eggplant", delete "a", insert --an--, therefor.

Signed and Sealed this
Twenty-sixth Day of September, 2023

Katherine Kelly Vidal
*Director of the United States Patent and Trademark Office*